United States Patent [19]

Wakimasu et al.

[11] Patent Number: 5,306,808
[45] Date of Patent: Apr. 26, 1994

[54] PEPTIDE DERIVATIVES HAVING VASODILATING ACTIVITY

[75] Inventors: Mitsuhiro Wakimasu; Takashi Kikuchi; Kazuki Kubo, all of Tsukuba, Japan

[73] Assignee: Takeda Chemical Industries, Ltd., Osaka, Japan

[21] Appl. No.: 768,269

[22] PCT Filed: Feb. 12, 1991

[86] PCT No.: PCT/JP91/00165
§ 371 Date: Oct. 17, 1991
§ 102(e) Date: Oct. 17, 1991

[87] PCT Pub. No.: WO91/13089
PCT Pub. Date: Sep. 5, 1991

[51] Int. Cl.$^5$ .............................. C07K 7/10
[52] U.S. Cl. .................................... 530/326
[58] Field of Search ................. 530/326; 514/13

[56] References Cited
PUBLICATIONS

Inoue, A. et al. PNAS 86; 2863-2867; Apr. 1989.
Randall, M. D. et al. Br. J. Pharmacol. 98; 685-699 (1989).

*Primary Examiner*—Lester L. Lee
*Attorney, Agent, or Firm*—David G. Conlin; David S. Resnick

[57] ABSTRACT

Disclosed are a peptide derivative represented by the formula [I] or a pharmaceutically acceptable salt thereof:

H-Cys-A-W-B-C-D-E-Asp-X-Glu-Y-Val-Tyr-F-Cys-His-Leu-Z-
-Ile-Ile-Trp-OH wherein A, B, C, D, E and F each represent amino acid residues, and satisfy any one condition of (i) A=Ser, B=Ser, C=Ser, D=Leu, E=Met and F=Phe, (ii) A=Ser, B=Ser, C=Ser, D=Trp, E=Leu and F=Phe, and (iii) A=Thr, B=Phe, C=Thr, D=Tyr, E=Lys and F=Tyr; and W, X, Y and Z each represent amino acid residues, and satisfy any one condition of (i) at least one of W and Y is an amino acid residue other than an L-alanine residue or other than an L-cysteine residue, (ii) X is an amino acid residue other than an L-Lysine residue, and (iii) Z is an amino acid residue other than an L-aspartic acid residue; (2) a method for producing the peptide derivative or the salt thereof; and (3) an agent for improving a circulatory function mainly comprising the peptide derivative or the salt thereof, such as a vasodilator or a vasoconstrictor.

1 Claim, No Drawings

PEPTIDE DERIVATIVES HAVING VASODILATING ACTIVITY

BACKGROUND OF THE INVENTION

The present invention relates to novel endothelin derivatives which are expected to be useful as therapeutic drugs such as agents for improving circulatory functions (for example, therapeutic agents for hypertension or hypotension), therapeutic agents for cardiac or cerebral circulatory diseases (for example, cardiac infarction), and therapeutic agents for renal diseases (for example, acute renal insufficiency); methods for producing the same; and agents for improving circulatory functions mainly comprising the same.

Endothelin (ET) is a vasoconstrictive peptide composed of 21 amino acid residues which was isolated from the culture supernatant of the endothelial cells of porcine aortas and whose structure was determined by M. Yanagisawa et al. in 1988 [M. Yanagisawa et al., *Nature* 332, 411-415 (1988)]. After that, the research on genes coding for endothelin revealed the presence of peptides similar to endothelin in structure. These peptides are named endothelin-1 (ET-1), endothelin-2 (ET-2) and endothelin-3 (ET-3), respectively, and their structures are as follows:

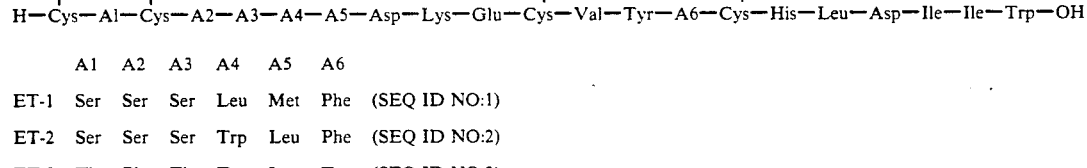

|      | A1  | A2  | A3  | A4  | A5  | A6  |             |
|------|-----|-----|-----|-----|-----|-----|-------------|
| ET-1 | Ser | Ser | Ser | Leu | Met | Phe | (SEQ ID NO:1) |
| ET-2 | Ser | Ser | Ser | Trp | Leu | Phe | (SEQ ID NO:2) |
| ET-3 | Thr | Phe | Thr | Tyr | Lys | Tyr | (SEQ ID NO:3) |

(All of the amino acids constituting ET-1, ET-2 and ET-3 take the L-form.) (Inoue et al., *Proc. Natl. Acad. Sci. U.S.A.* 86, 2863-2867)

The above-mentioned peptides of the endothelin family exist in vivo and have vasopressor activity. For this reason, these peptides are anticipated to be intrinsic factors responsible for the control of circulatory systems, and deduced to be related to hypertension, cardiac or cerebral circulatory diseases (for example, cardiac infarction) and renal diseases (for example, acute renal insufficiency).

If antagonists or agonists of the above-mentioned peptides are obtained, they are considered not only useful for elucidation of the functional mechanism of these peptides, but also they are most likely to be used as effective therapeutic drugs for these diseases. At present, however, no reports are found that an effective antagonist to endothelin has been obtained. Further, it is another subject of the present invention to discover a substance which enhances the activity of endothelin.

SUMMARY OF THE INVENTION

The present inventors conducted intensive investigation, using the action of suppressing or enhancing strong vascular smooth muscle constrictor activity due to endothelin as an indication, and synthesized endothelin analogues by the replacement of amino acids of endothelin. As a result, the present inventors found that novel endothelin derivatives of the present invention had the antagonist action or the agonist action to endothelin, thus completing the present invention.

Namely, the present invention provides (1) a peptide derivative represented by general formula [I] or a pharmaceutically acceptable salt thereof:

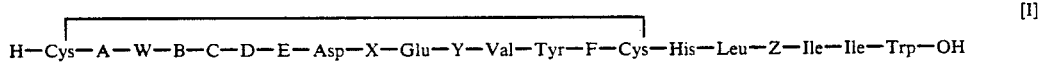

[I]

wherein A, B, C, D, E and F each represent amino acid residues, and satisfy any one condition of (i) A=Ser, B=Ser, C=Ser, D=Leu, E=Met and, F=Phe (SEQ. ID NO:4), (ii) A=Ser, B=Ser, C=Ser, D=Trp, E=Leu and F=Phe (SEQ. ID NO:5), and (iii) A=Thr, B=Phe, C=Thr, D=Tyr, E=Lys and F=Tyr (SEQ. ID NO.6); and W, X, Y and Z each represent amino acid residues, and satisfy any one condition of (i) at least one of W and Y is an amino acid residue other than an L-alanine residue or other than an L-cysteine residue, (ii) X is an amino acid residue other than an L-lysine residue, and (iii) Z is an amino acid residue other than an L-aspartic acid residue;

(2) a method for producing the peptide derivative represented by general formula [I] or the salt thereof, which comprises subjecting a peptide derivative represented by general formula [II] or a salt thereof to oxidation reaction:

H-Cys-A-W-B-C-D-E-Asp-X-Glu-Y-Val-Tyr-F-Cys-His-Leu-Z-Ile-Ile-Trp-OH  [II]

wherein A, B, C, D, E and F each represent amino acid residues, and satisfy any one condition of (i) A=Ser, B=Ser, C=Ser, D=Leu, E=Met and F=Phe, (ii) A=Ser, B=Ser, C=Ser, D=Trp, E=Leu and F=Phe, and (iii) A=Thr, B=Phe, C=Thr, D=Tyr, E=Lys and F=Tyr; and W, X, Y and Z each represent amino acid residues, and satisfy any one condition of (i) at least one of W and Y is an amino acid residue other than an L-alanine residue or other than an L-cysteine residue, (ii) X is an amino acid residue other than an L-lysine residue, and (iii) Z is an amino acid residue other than an L-aspartic acid residue; and (3) an agent for improving a circulatory function mainly comprising the peptide derivative represented by general formula [I], such as a vasodilator or a vasoconstrictor.

DESCRIPTION OF THE PREFERRED EMBODIMENTS

The vasodilators include

Cys—Ser—Phe—Ser—Ser—Leu—Met—Asp—Lys—Glu—Phe—Val—Tyr—Phe—Cys—His—Leu—Asp—Ile—Ile—Trp
(SEQ ID NO: 9)  (the compound of Example 1), Cys—Ser—Phe—Ser—Ser—Leu—Met—Asp—Lys—Glu—Ala—Val—Tyr—Phe—Cys—His—Leu—Asp—Ile—Ile—Trp
(SEQ ID NO: 10)  (the compound of Example 2), Cys—Ser—Trp—Ser—Ser—Leu—Met—Asp—Lys—Glu—Ala—Val—Tyr—Phe—Cys—His—Leu—Asp—Ile—Ile—Trp
(SEQ ID NO: 21)  (the compound of Example 13), Cys—Ser—Ala—Ser—Ser—Leu—Met—Asp—Lys—Glu—Ala—Val—Tyr—Phe—Cys—His—Leu—Leu—Ile—Ile—Trp
(SEQ ID NO: 30)  (the compound of Example 22), Cys—Ser—Ala—Ser—Ser—Leu—Met—Asp—Lys—Glu—Ala—Val—Tyr—Phe—Cys—His—Leu—Phe—Ile—Ile—Trp
(SEQ ID NO: 31)  (the compound of Example 23), Cys—Ser—Cys—Ser—Ser—Leu—Met—Asp—Lys—Glu—Cys—Val—Tyr—Phe—Cys—His—Leu—Leu—Ile—Ile—Trp
(SEQ ID NO: 34)  (the compound of Example 26), Cys—Ser—Cys—Ser—Ser—Leu—Met—Asp—Lys—Glu—Cys—Val—Thr—Phe—Cys—His—Leu—Val—Ile—Ile—Trp
(SEQ ID NO: 35)  (the compound of Example 27), Cys—Ser—Cys—Ser—Ser—Leu—Met—Asp—Lys—Glu—Cys—Val—Tyr—Phe—Cys—His—Leu—Nva—Ile—Ile—Trp
(SEQ ID NO: 38)  (the compound of Example 31), Cys—Ser—Cys—Ser—Ser—Leu—Met—Asp—Lys—Glu—Cys—Val—Tyr—Phe—Cys—His—Leu—Nle—Ile—Ile—Trp
(SEQ ID NO: 39)  (the compound of Example 32), Cys—Ser—Cys—Ser—Ser—Leu—Met—Asp—Lys—Glu—Cys—Val—Tyr—Phe—Cys—His—Leu—Ile—Ile—Ile—Trp
(SEQ ID NO: 50)  (the compound of Example 43), Cys—Ser—Cys—Ser—Ser—Leu—Met—Asp—Lys—Glu—Cys—Val—Tyr—Phe—Cys—His—Leu—γ—Leu—Ile—Ile—Trp
(SEQ ID NO: 52)  (the compound of Example 45), and Cys—Ser—Cys—Ser—Ser—Leu—Met—Asp—Lys—Glu—Cys—Val—Tyr—Phe—Cys—His—Leu—Glu—Ile—Ile—Trp
(SEQ ID NO: 53)  (the compound of Example 46).

The vasoconstrictors include

Cys—Ser—Cys—Ser—Ser—Leu—Met—Asp—Lys—Glu—Cys—Val—Tyr—Phe—Cys—His—Leu—Ala—Ile—Ile—Trp
(SEQ ID NO:33)  (the compound of Example 25), Cys—Ser—Cys—Ser—Ser—Leu—Met—Asp—Lys—Glu—Cys—Val—Tyr—Phe—Cys—His—Leu—Gly—Ile—Ile—Trp
(SEQ ID NO:36)  (the compound of Example 28), Cys—Ser—Cys—Ser—Ser—Leu—Met—Asp—Lys—Glu—Cys—Val—Tyr—Phe—Cys—His—Leu—Ser—Ile—Ile—Trp (SEQ ID NO:41) (the compound of Example 34),

```
  ┌─────────────────────────────────────────────────────────────────┐
Cys—Ser—Val—Ser—Ser—Leu—Met—Asp—Lys—Glu—Ala—Val—Tyr—Phe—Cys—His—Leu—Asp—Ile—Ile—Trp
```
(SEQ ID NO:48) (the compound of Example 41), and

```
  ┌──────┬──────────────────────────────────────────────────────────┐
Cys—Ser—Cys—Ser—Ser—Leu—Met—Asp—Lys—Glu—Cys—Val—Tyr—Phe—Cys—His—Leu—Thr—Ile—Ile—Trp
```
(SEQ ID NO:58) (the compound of Example 51).

In this specification, amino acids and peptides are indicated by the abbreviations commonly used in the art or adopted by the IUPAC-IUB Commission on Biochemical Nomenclature. For example, the following abbreviations are also used:

| | |
|---|---|
| Ala | Alanine |
| Asp | Aspartic acid |
| Cys | Cysteine |
| Glu | Glutamic acid |
| His | Histidine |
| Ile | Isoleucine |
| Leu | Leucine |
| Lys | Lysine |
| Met | Methionine |
| Phe | Phenylalanine |
| Ser | Serine |
| Thr | Threonine |
| Trp | Tryptophan |
| Tyr | Tyrosine |
| Tyr (Et) | O-Ethyltyrosine |
| Val | Valine |

| | |
|---|---|
| Nal (1) | 1-Naphthylalanine |
| Nal (2) | 2-Naphthylalanine |
| Cha | Cyclohexylalanine |
| Thi | β-2-Thienylalanine |
| Phe (4F) | 4-Fluorophenylalanine |
| Phg | Phenylglycine |
| Cyt | Cystine |
| Abu | 2-Aminobutyric acid |
| Nva | Norvaline |
| Nle | Norleucine |
| t-Leu | Tertiary-leucine |
| γ-Leu | γ-Methylleucine |

Protective groups and reagents commonly used in this specification are indicated by the following abbreviations:

| | |
|---|---|
| Boc | t-Butyloxycarbonyl |
| Bzl | Benzyl |
| Brz | 2-Bromobenzyloxycarbonyl |
| Clz | 2-Chlorobenzyloxycarbonyl |
| Tos | p-Toluenesulfonyl |
| Dnp | 2,4-Dinitrophenyl |
| OcHex | Cyclohexyl ester |
| For | Formyl |
| MeBzl | 4-Methylbenzyl |
| Acm | Acetamidomethyl |
| TFA | Trifluoroacetic acid |
| HF | Anhydrous hydrogen fluoride |
| HOBt | 1-Hydroxybenzotriazole |
| DMF | N,N-Dimethylformamide |

In the present invention, the aminoacid residue represented by W, X, Y or Z may be either a natural amino acid residue or an unnatural aminoacid residue, and may be any of the L-, D- and DL-forms. Accordingly, W, X, Y and Z can also be expressed as

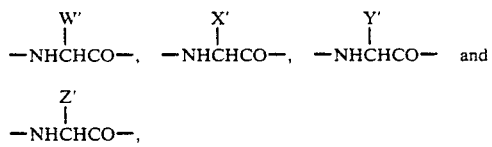

respectively. The compound of formula [I] can be represented by formula [I']:

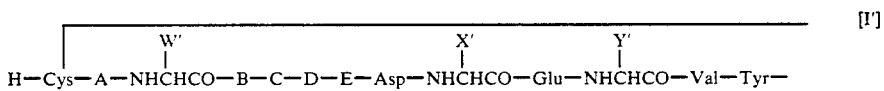

wherein each of W', X', Y' and Z' represents a hydrogen atom or a hydrocarbon group which may be substituted and has 1 to 15 carbon atoms. The hydrocarbon groups having 1 to 15 carbon atoms include aliphatic hydrocarbon groups, aromatic hydrocarbon groups and aliphatic-aromatic hydrocarbon groups.

Examples of the substituents include sulfur substituents (such as thione, mercapto, methylthio, ethylthio, n-propylthio, isopropylthio, n-butylthio, isobutylthio, t-butylthio, phenylthio, cyclopentylthio and cyclohexylthio), oxygen substituents (such as ketone, hydroxy, methoxy, ethoxy, n-propoxy, isopropoxy, n-butoxy, isobutoxy, t-butoxy, n-pentyloxy, cyclopentyloxy, n-hexyloxy, cyclohexyloxy, phenoxy and benzyloxy), nitrogen substituents (such as amino, N-methylamino, N-ethylamino, N-n-propylamino, N-isopropylamino, N-n-butylamino, N-isobutylamino, N-t-butylamino, N-n-pentylamino, N-n-hexylamino, N-cyclohexylamino, N,N-dimethylamino, N,N-diethylamino, N,N-di-n-propylamino, N,N-di-isopropylamino, N,N-di-n-butylamino, N,N-diisobutylamino, N,N-di-t-butylamino, N,N-di-n-pentylamino, N,N-di-n-hexylamino, N,N-dicyclohexylamino, nitro and guanidino), halogen substituents (such as chloro, bromo and fluoro) and heterocyclic substituents (such as pyrrolidino, piperidino, indolyl, imidazolyl, thienyl and furyl).

The aliphatic hydrocarbon groups may be straight-chain, branched-chain or cyclic groups saturated or unsaturated. Examples thereof include methyl, ethyl, n-propyl, isopropyl, n-butyl, isobutyl, t-butyl, n-pentyl, isopentyl, neopentyl, cyclopentyl, n-hexyl, cyclohexyl, n-heptyl, cycloheptyl, n-octyl, n-nonyl, n-decyl, cyclopentylmethyl and cyclohexylmethyl. The substituted aliphatic hydrocarbon groups include methylthiomethyl, ethylthiomethyl, n-propylthiomethyl, isopropylthiomethyl, n-butylthiomethyl, t-butylthiomethyl, 2-methylthioethyl, 2-ethylthioethyl, 2-t-butylthioethyl, mercaptomethyl, 1-mercaptoethyl, 2-mercaptoethyl phenylthiomethyl, 1-phenylthioethyl, 2-phenylthioethyl, benzylthiomethyl, 4-methoxyphenylthiomethyl, benzylthiomethyl, 4-methoxybenzylthiomethyl, 4-methylbenzylthiomethyl, 4-nitrobenzylthiomethyl, 4-pyridylmethylthiomethyl, hydroxymethyl, 1-hydroxyethyl, 2-hydroxyethyl, methoxymethyl, ethoxymethyl, n-propoxymethyl, isopropoxymethyl, n-butoxymethyl, t-butoxymethyl, n-pentyloxymethyl, cyclopentyloxymethyl, n-hexyloxymethyl, cyclohexyloxymethyl, 1-methoxyethyl, 1-ethoxyethyl, 1-propoxyethyl, 1-isopropoxyethyl, 1-n-butoxyethyl, 1-isobutoxyethyl, 1-t-butoxyethyl, phenoxymethyl, 1-phenoxyethyl, 2-phenoxyethyl, benzyloxymethyl, 2-benzyloxyethyl, carboxymethyl, 1-carboxyethyl, 2-carboxyethyl, methoxycarbonylmethyl, ethoxycarbonylmethyl, n-propoxycabonylmethyl, isopropoxycarbonylmethyl, n-butoxycarbonylmethyl, isobutoxycarbonylmethyl, t-butoxycarbonylmethyl, n-pentyloxycarbonylmethyl, cyclopentyloxycarbonylmethyl, n-hexyloxycarbonylmethyl, cyclohexyloxycarbonylmethyl, cycloheptyloxycarbonylmethyl, cyclooctyloxycarbonylmethyl, carboxyethyl, methoxycarbonylethyl, ethoxycarbonylethyl, n-propoxycarbonylethyl, isopropoxycarbonylethyl, n-butoxycarbonylethyl, isobutoxycarbonylethyl, t-butoxycarbonylethyl, n-pentyloxycarbonylethyl, cyclopentyloxycarbonylethyl, n-hexyloxycarbonylethyl, cyclohexyloxycarbonylethyl, cycloheptyloxycarbonylethyl, cyclooctyloxycarbonylethyl, 2-aminoethyl, 2-(N-methylamino)ethyl, 2-(N,N-dimethylamino)ethyl, 3-aminopropyl, 3-(N,N-diethylamino)propyl, 2-guanidinoetyl, 3-guanidinopropyl, aminocarbonylmethyl, n-methylaminocarbonylmethyl, N-ethylaminocarbonylmethyl, N-n-propylaminocarbonylmethyl, N-isopropylaminocarbonylmethyl, N-n-butylaminocarbonylmethyl, N-isobutylaminocarbonylmethyl, N-t-butylaminocarbonylmethyl, N-n-pentylaminocarbonylmethyl, N-isopentylaminocarbonylmethyl, N-neopentylaminocarbonylmethyl, N-n-hexylaminocarbonylmethyl, N-cyclohexylaminocarbonylmethyl, N,N-dimethylaminocarbonylmethyl, N,N-diethylaminocarbonylmethyl, N,N-di-n-propylaminocarbonylmethyl, N,N-diisopropylaminocarbonylmethyl, N,N-di-n-butylaminocarbonylmethyl, N,N-diisobutylaminocarbonylmethyl, N,N-di-t-butylaminocarbonylmethyl, N,N-di-n-pentylaminocarbonylmethyl, N,N-diisopentylaminocarbonylmethyl, N,N-dineopentylaminocarbonylmethyl, N,N-di-n-hexylaminocarbonylmethyl, N,N-dicyclohexylaminocarbonylmethyl, pyrrolidinocarbonylmethyl, piperidinocarbonylmethyl, aminocarbonylethyl, N-methylaminocarbonylethyl, N-ethylaminocarbonylethyl, N-n-propylaminocarbonylethyl, N-isopropylaminocarbonylethyl, N-n-butylaminocarbonylethyl, N-isobutylaminocarbonylethyl, N-t-butylaminocarbonylethyl, N-n-pentylaminocarbonylethyl, N-cyclopentylaminocarbonylethyl, N-n-hexylaminocarbonylethyl, N-cyclohexylaminocarbonylethyl, N,N-dimethylaminocarbonylethyl, N,N-diethylaminocarbonylethyl, N,N-di-n-propylaminocarbonylethyl, N,N-diisopropylaminocarbonylethyl, N,N-di-n-butylaminocarbonylethyl, N,N-diisobutylaminocarbonylethyl, N,N-di-t-butylaminocarbonylethyl, N,N-di-n-pentylaminocarbonylethyl, N,N-dicyclopentylaminocarbonylethyl, N,N-di-n-hexylaminocarbonylethyl, N,N-dicyclohexylaminocarbonylethyl, 3-indolylmethyl, 4-imidazolylmethyl, 2-thienylmethyl, 2-furylmethyl, pyrrolidinocarbonylethyl and piperidinocarbonylethyl.

Examples of the aromatic hydrocarbon groups and aliphatic-aromatic hydrocarbon groups include phenyl, 1-naphthyl, 2-naphthyl, phenylmethyl, 1-phenylethyl, 2-phenylethyl, 1-naphthylmethyl, 2-naphthylmethyl and 9-anthranylmethyl. Examples of the substituted aromatic hydrocarbon groups and aliphatic-aromatic hydrocarbon groups include 4-hydroxyphenyl, 4-hydroxyphenylmethyl, 4-methoxyphenylmethyl, 4-ethoxyphenylmethyl, 4-n-proproxyphenylmethyl, 4-isopropoxyphenylmethyl, 4-n-butoxyphenylmethyl, 4-isobutoxyphenylmethyl, 4-t-butoxyphenylmethyl, 4-n-pentyloxyphenylmethyl, 4-cyclopentyloxyphenylmethyl, 4-n-hexyloxyphenylmethyl, 4-cyclohexyloxyphenylmethyl, 4-aminophenylmethyl, 4-dimethylaminophenylmethyl, 4-diethylaminophenylmethyl, 4-di-n-propylaminophenylmethyl, 4-diisopropylaminophenylmethyl, 4-di-n-butylaminophenylmethyl, 4-pyrrolidinophenylmethyl, 4-piperidinophenylmethyl, 4-nitrophenylmethyl, 4-fluorophenylmethyl, 3-fluorophenytlmethyl, 2-fluorophenylmethyl, 4-chlorophenylmethyl, 3-chlorophenylmethyl and 2-chlorophenylmethyl.

The pharmaceutically acceptable salts of the compounds represented by formula [I]or [I'] include sodium salts and calcium salts as well as addition salts of inorganic acids such as hydrochlorides, sulfates and phosphates, and salts of organic acids such as acetates, propionates, citrates, tartrates, malates and oxalates. The peptides of the present invention represented by formula [I] or [I'] can be produced by methods for peptide synthesis known in the art, which may be either solid phase synthesis methods or liquid phase synthesis methods. Examples of such methods for peptide synthesis include methods described in M. Bodansky and M. A. Ondetti, *Peptide Synthesis*, Interscience, New York (1966); F. M. Finn and K. Hofmann, *The Proteins*, Vol. 2, edited by H. Nenrath and R. L. Hill, Academic Press, New York, (1976); N. Izumiya et al., *Peptide Gosei no Kiso to Jikken* (Fundamentals and Experiments of Peptide Synthesis), Maruzen (1985); H. Yazima, S. Sakakibara et al., *Seikagaku Jikken Koza* (Course of Biochemical Experiments) 1, edited by Biochemical Society of Japan, Tokyo Kagaku Dojin (1977); H. Kimura et al., Zoku Seikagaku Jikken Koza(Course of Biochemical Experiments, second series), 2, edited by Biochemical Society of Japan, Tokyo Kagaku Dojin (1987); and J. M. Stewart and J. D. Young, *Solid Phase Peptide Synthesis*, Pierce Chemical Company,. Illinois (1984), such as azide methods, chloride methods, acid anhydride methods, mixed acid anhydride methods, DCC methods, active ester methods, methods using Woodward reagent K, carbodiimidazole methods, oxidation-reduction methods, DCC/HONB methods and methods using BOP reagents.

The compound of the present invention represented by formula [I] or [I'] can be produced by condensing a raw material having a reactive carboxyl group corresponding to one of two kinds of fragments which are separated at any position of its peptide bond with a raw material having a reactive amino group corresponding to the other fragment, and then, eliminating a protective group by methods known in the art, if the resulting condensed product has any protective group.

In particular, in the solid phase synthesis methods, an amino acid whose functional group not to be related to reaction is protected is combined with an insoluble carrier such as a Pam resin through an carboxyl group of the amino acid. After elimination of the protective group, an amino acid whose functional group not to be related to reaction is protected is condensed therewith. This procedure is repeated until a desired protected peptide is obtained. Then, the protective group is eliminated and the bond with the insoluble carrier is concurrently broken by methods known in the art such as hydrogen fluoride treatment, trifluoromethanesulfonic acid treatment and trifluoroacetic acid treatment, whereby the compound of the present invention can be produced.

In some cases, the compound represented by formula [II] or [II'] may be synthesized by the above-mentioned methods, and then oxidized by methods known in the art to synthesize the compound represented by formula [I] or [I'].

The hydroxyl group of serine can be protected, for example, by esterification or etherification. Examples of groups suitable for this esterification include lower alkanoyl groups such as acetyl, aroyl groups such as benzoyl, and carbonic acid-derived groups such as benzyloxycarbonyl and ethyloxycarbonyl. Examples of groups suitable for the etherification include benzyl, tetrahydropyranyl and t-butyl. However, the hydroxyl group of serine is not always required to be protected.

Examples of the protective groups for the phenolic hydroxyl group of tyrosine include benzyl, 2,6-cyclobenzyl, 2-nitrobenzyl, 2-bromobenzyloxycarbonyl and t-butyl. However, the phenolic group of tyrosine is not always required to be protected.

Methionine may be protected in the form of sulfoxides.

The protective groups for the imidazole ring of histidine include p-toluenesulfonyl, 4-methoxy-2,3,6-trimethylbenzenesulfonyl, 2,4-dinitrophenyl, benzyloxymethyl, t-butoxymethyl, t-butoxycarbonyl, trityl and 9-fluorenylmethyloxycarbonyl. However, the imidazole ring is not always required to be protected.

The protective groups for the indole ring of tryptophan include fornyl, 2,4,6-trimethylbenzensulfonyl, 2,4,6-trimethoxybenzenesulfonyl, 4-methoxy-2,3,6-trimethylbenzenesulfonyl, 8,8,8-trichloroethyloxycarbonyl and diphenylphosphinothioyl. However, the in-

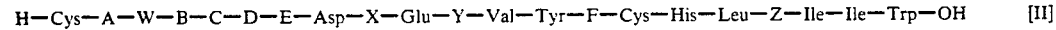

H—Cys—A—W—B—C—D—E—Asp—X—Glu—Y—Val—Tyr—F—Cys—His—Leu—Z—Ile—Ile—Trp—OH   [II]

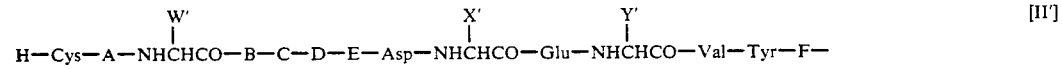

$$\begin{array}{ccc} W' & X' & Y' \\ | & | & | \end{array}$$

H—Cys—A—NHCHCO—B—C—D—E—Asp—NHCHCO—Glu—NHCHCO—Val—Tyr—F—   [II']

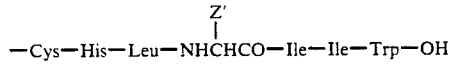

$$\begin{array}{c} Z' \\ | \end{array}$$

—Cys—His—Leu—NHCHCO—Ile—Ile—Trp—OH

When at least two thiol groups are contained as W', X', Y' and Z', a compound in which these thiol groups are oxidized to form a disulfide bond is also included in the scope of the present invention.

Protection of the functional groups not to be related to the reaction of the raw materials and the protective groups, elimination of the protective groups, and activation of the functional groups related to the reaction can also be suitably selected from groups or methods known in the art.

Examples of the protective groups for the amino group of the raw materials include carbobenzoxy, t-butyloxycarbonyl, t-amyloxycarbonyl, isobornyloxycarbonyl, 4-methoxybenzyloxycarbonyl, 2-chlorobenzyloxycarbonyl, adamantyloxycarbonyl, trifluoroacetyl, phthalyl, formyl, 2-nitrophenylsulfenyl, diphenylphosphinothioyl and 9-fluorenylmethyloxycarbonyl. The protective groups for the carboxyl group include, for example, alkyl esters (such as esters of methyl, ethyl, propyl, butyl, t-butyl, cyclopentyl, cyclohexyl, cycloheptyl, cyclooctyl and 2-adamantyl), benzyl esters, 4-nitrobenzyl esters, 4-methoxybenzyl esters, 4-chlorobenzyl esters, benzhydryl esters, phenacyl esters, carbobenzoxyhydrazide, t-butyloxycarbonylhydrazide and tritylhydrazide.

Examples of the protective groups for the thiol group of cysteine include 4-methoxybenzyl, 4-methylbenzyl, benzyl, t-butyl, adamantyl, trityl, acetamidomethyl, carbomethoxysulfenyl, 3-nitro-2-pyridinesulfenyl and trimethylacetamidomethyl.

dole ring is not always required to be protected.

Examples of the activated carboxyl groups of the raw materials include acid anhydrides, azide and active esters (esters of alcohols such as pentachlorophenol, 2,4,5-trichlorophenol, 2,4-dinitrophenol, cyanomethyl alcohol, p-nitrophenol, N-hydroxy-5-norbornene-2,3-dicarboxyimide, N-hydroxysuccinimide, N-hydroxyphthalimide and N-hydroxybenztriazole. Examples of the activated amino acid groups include cooresponding phosphoric acid amides.

Condensation reaction can be conducted in the presence of a solvent or solvents. The solvent or solvents can be appropriately selected from the solvents known to be capable of being used in peptide condensation reaction. Examples of the solvents include anhydrous or hydrous dimethylformamide, dimethyl sulfoxide, pyridine, chloroform, dioxane, dichloromethane, tetrahydrofuran, acetonitrile, ethyl acetate, N-methylpyrrolidone and appropriate mixtures thereof.

The reaction temperature is appropriately selected from the temperature range known to be capable of being used in peptide bond-forming reaction, usually from the range of about −20° to about 30° C.

Then, the protected peptide or the protected peptide resin thus obtained is subjected to protective group-eliminating reaction. Although this reaction varies depending on the kind of protective group to be used, it is in any event industrially advantageous to eliminate all protective groups in one step without affecting the peptide bonds. The protective groups are therefore employed, preliminarily taking this point into account. As to the cysteine-containing peptides, it is more advantageous from the viewpoint of the ease of purification in some cases to eliminate the protective groups in two steps, namely, to eliminate the protective groups other than the protective groups for the thiol group first, followed by elimination of the protective groups for the thiol group. The protective groups for the thiol group used in such cases include acetamidomethyl, 3-nitro-2-pyridinesulfenyl and trimethylacetamidomethyl.

Methods for eliminating the protective groups include, for example, reduction with sodium in liquid ammonia, in addition to acid treatment with anhydrous hydrogen fluoride, methanesulfonic acid, trifluoromethanesulfonic acid, trifluoroacetic acid or mixtures thereof. The protective group-eliminating reaction by the above-mentioned acid treatment is generally conducted at a proper temperature of $-20°$ to $40°$ C. In the acid treatment, it is effective to add a cation trapping agent such as anisole, phenol, thioanisole, m-cresol, p-cresol, dimethylsulfide, 1,4-butanedithiol or 1,2-ethanedithiol. For the protective groups for the thiol group stable to the acid treatment, such as acetamidomethyl and 3-nitro-2-pyridinesulfenyl, the former can be eliminated with iodine or mercury acetate, and the latter can be eliminated with mercaptoethanol. The 2,4-dinitrophenyl group used as the protective group for the imidazole ring of histidine is eliminated by thiophenol treatment, and the formyl group used as the protective group for the indole ring of tryptophan is also eliminated by alkali treatment using dilute sodium hydroxide, dilute ammonia or the like, in addition to the above-mentioned elimination by the acid treatment in the presence of 1,2-ethanedithiol, 1,4-butanedithiol or the like.

When the peptide obtained by eliminating the protective groups of the protected peptide in this manner is the thiol peptide represented by formula [II] or [II'] the thiol peptide is subjected to oxidation. The oxidation methods include the methods of oxidizing the thiol peptide in a solvent such as water with air, potassium ferricyanide, iodine, diiodoethane or the like. It is desirable that the above-mentioned oxidation reaction is generally conducted by a high dilution method at a proper temperature of about $0°$ to about $40°$ C. at a pH of about 6 to about 8.5.

After completion of the reaction, the peptide derivative represented by formula [I] or [I'] thus obtained is collected by peptide separating means such as extraction, distribution, reprecipitation, recrystallization, column chromatography and high performance liquid chromatography.

The peptide derivative of the present invention represented by formula [I[or [I'] may also be obtained by methods known in the art as salts such as the sodium salt, the potassium salt, the calcium salt and the magnesium salt, or as acid addition salts, particularly pharmaceutically acceptable acid addition salts. Examples thereof include salts of inorganic acids (such as hydrochloric acid, sulfuric acid and phosphoric acid) or organic acids (such as acetic acid, propionic acid, citric acid, tartaric acid, malic acid, oxalic acid and methanesulfonic acid).

The pharmacological action of the peptide derivatives of the present invention will hereinafter be described.

(1) Assay of Constriction Suppressing Activity to Porcine Coronary Smooth Muscles Each of helical strips 2 mm $\times$ 15 mm prepared from the coronary right ramus circumflexus from which the adventitial connective tissues and the endothelial cells were removed was set to each of 4 ml organ baths. Its tension was detected by a force displacement transducer UL-10GR (Minebea), and recorded by a polygraph (NEC Sanei). The organ baths were maintained at $37°$ C., and filled with a Krebs-Henseleit solution (composition: 118 mM NaCl, 4.7 mM KCl, 2.5 mM $CaCl_2$, 1.2 mM $KH_2PO_4$, 25.0 mM $NaHCO_3$, 1.2 mM $MgSO_4$, 10.0 mM glucose) gassed with 95% $O_2$ and 5% $CO_2$.

A tension of 1.25 to 1.5 g was applied to each of the strips, followed by equilibration for 1.5 hours. 60 mM KCl was repeatedly applied thereto at intervals of 30 minutes until the constriction response became constant. After additional equilibration for 1.5 hours, a sample for assay was given. The constriction of the strips was normalized by the constriction response of the individual strips to 60 mM KCl and statistically processed.

The suppressing activity was assayed by giving $10^{-9}$ M endothelin-1 about 15 minutes after the compound having a predetermined concentration was given, and comparing the constriction thereof with that of a control sample. The results thereof are shown in Table 1.

TABLE 1

| Example No. | Sample | Suppressing activity to ET-1 $\frac{(control - sample)}{control} \times 100$ (%) |
|---|---|---|
| 1 | [Phe$^{3,11}$]-ET-1 | 77 |
| 2 | [Phe$^3$, Ala$^{11}$]-ET-1 | 87 |
| 3 | [Ala$^3$, Phe$^{11}$]-ET-1 | 56 |

Control: Constriction due to $10^{-9}$ M ET-1
Sample: Constriction due to $10^{-9}$ M ET-1 in the presence of $10^{-5}$ M sample The novel peptide derivatives of the present invention represented by formula [I] and parts of the salts thereof showed the activity of suppressing the constriction due to endothelin in porcine coronary smooth muscles. Such a case has not been reported yet.

Hence, the peptide derivatives of the present invention represented by formula [I] or parts of the salts thereof can be used for the treatment of hypertension, cardiac infarction or acute renal insufficiency of mammals such as mice, rate, rabbits, dogs, cats, pigs and humans. (2) As to the antagonist property or the agonist property of the peptide derivatives of present invention to endothelin, the affinity for an endothelin receptor and the constrictor activity to porcine coronary smooth muscles (according to the method described in (1) described above) were assayed. The results thereof are shown in Table 2. The affinity for the receptor was assayed by the following method.

Assay of Affinity for Receptor

A membrane fraction prepared from the porcine heart was diluted to 0.15 mg/ml by using a buffer solution [PBS (pH 7.4) containing 0.5 mM $CaCl_2$, 1.0 mM $MgCl_2$, 0.02% $NaN_3$, 0.1% BSA (fraction V, Sigma), 0.1 mM PMSF and 0.1 $\mu$g/ml pepstatin (binding buffer)] for assay, and 100 $\mu$l of the resulting suspension of the membrane fraction was poured into each assay tube to use for assay. To this suspension of the membrane fraction were added 2 $\mu$l of an endothelin-1 solution labeled with 5 μM radioactive iodine. Further, 3 μl of a test peptide solution was added thereto, followed by maintenance at a temperature of 25° C. for 1 hour. Then, the resulting suspension was diluted with 900 μl of the buffer solution for assay cooled with ice, and thereafter separated into a supernatant and a precipitate by centrifugation at 12,000×g for 10 minutes. Cell membranes and an endothelin receptor embedded therein were contained in the precipitate, and radioactive iodine-labeled endothelin combined with the receptor was also recovered in the precipitate. Accordingly, the amount of radioactive iodine-labeled endothelin combined with the endothelin receptor was determined by measuring the amount of radioactive iodine contained in the precipitate with a gamma-ray counter. Compounds in which the affinity for the endothelin receptor is high and the maximum constriction is not high are antagonists. Contrary to this, compounds in which the affinity for the endothelin receptor is high and the maximum constriction is high are agonists.

The novel peptides of the present invention, when used as pharmaceutical drugs, can be safely administered orally or parenterally in the form of powders, granules, tablets, capsules, injections, suppositories, ointments or sustained release preparations, solely or in combination with pharmaceutically acceptable carriers, excipients or diluents. The derivatives of the present invention are mainly administered parenterally, for example, by intravenous or subcutaneous injection, intraventricular or intraspinal administration, nasotracheal administration or intrarectal administration. In some cases, however, they are administered orally.

The derivatives of the present invention are stable substances, and therefore, can be stored as physiological saline solutions. It is also possible to lyophilize the derivatives containing mannitol or sorbitol to store in ampuls and to dissolve the lyophilized derivatives in using them. The peptide derivatives of the present invention can be given in the free form, or in the form of alkali addition salts or acid addition salts thereof. For

TABLE 2

| Example No. | Compound | Receptor binding activity[1] (Relative potency) | Constrictor activity[2] (Relative potency) | Maximum Constriction (% 60 mM KCl) |
|---|---|---|---|---|
|  | ET-1 | 100[3] | 100[4] | 120 |
| Known* | [Ala$^{3,11}$]-ET-1 | 2.4 | 57 | 120 |
| 1 | [Phe$^{3,11}$]-ET-1 | 0.45 | <0.3 | 9 |
| 2 | [Phe$^3$,Ala$^{11}$]-ET-1 | 0.5 | <0.1 | 10 |
| 3 | [Ala$^3$,Phe$^{11}$]-ET-1 | 0.1 | <0.1 | 10 |
| 4 | [Trp$^3$,Ala$^{11}$]-ET-1 | 0.27 | <0.1 | 10 |
| 13 | [Trp3,Ala$^{11}$]-ET-1 | 2.5 | <0.1 | 6 |
| 21 | [Ala$^{3,11,18}$]-ET-1 | 1.59 | <0.1 | 6 |
| 22 | [Ala$^{3,11}$,Leu$^{18}$]-ET-1 | 1.27 | <0.1 | 3 |
| 23 | [Ala$^{3,11}$,Phe$^{18}$]-ET-1 | 1.27 | <0.1 | 8 |
| 25 | [Ala$^{18}$]-ET-1 | 9.1 | 7.8 | 62 |
| 26 | [Leu$^{18}$]-ET-1 | 2.4 | <0.1 | 0 |
| 27 | [Val$^{18}$]-ET-1 | 3.2 | <0.1 | 2 |
| 28 | [Gly$^{18}$]-ET-1 | 39.8 | 43 | 99 |
| 30 | [Abu$^{18}$]-ET-1 | 5.0 | <0.1 | 6 |
| 31 | [Nva$^{18}$]-ET-1 | 2.4 | <0.1 | 2 |
| 33 | [Phe$^{18}$]-ET-1 | 2.4 | <0.1 | 0 |
| 34 | [Ser$^{18}$]-ET-1 | 20.9 | 18 | 79 |
| 35 | [Asn$^{18}$]-ET-1 | 9.1 | <0.1 | 43 |
| 38 | [Leu$^{3,11}$]-ET-1 | 0.1 | <0.1 | 10 |
| 39 | [Val$^{3,11}$]-ET-1 | 0.59 | <0.1 | 34 |
| 41 | [Val$^3$,Ala$^{11}$]-ET-1 | 4.5 | 73 | 130 |
| 43 | [Ile$^{18}$]-ET-1 | 3.2 | <0.1 | 0 |
| 45 | [γ-Leu$^{18}$]-ET-1 | 1.0 | <0.1 | 3 |
| 46 | [Glu$^{18}$]-ET-1 | 3.2 | <0.1 | 6 |
| 51 | [Thr$^{18}$]-ET-1 | 100 | 26 | 76 |
| 52 | [Leu$^3$, Ala$^{11}$]-ET-1 | 0.35 | <0.1 | 6 |
| Ref1 | [Ala$^{3,11}$,desHis$^{16}$]-ET-1 | 0 |  |  |

*J. Cardiovascular Pharmacology 13, S197 (1989)
[1] Porcine myocardial membrane fraction
[2] Porcine coronary artery
[3] IC$_{50}$ = 2.0 × 10$^{-9}$ M, IC$_{50}$ represents the concentration of a sample required to prevent 50% of the binding of I$^{125}$-ET-1 to the porcine myocardial membrane fraction.
[4] EC$_{50}$ (% KCl) = 1.6 × 10$^{-9}$ M, EC$_{50}$ represents the concentration of a sample which induces 50% of the constriction of the porcine coronary artery due to 60 mM KCl.

As described above, the peptide derivatives of the present invention represented by formula [I] or the salts thereof have the properties as the antagonists or the agonists of endothelin, and can be used as agents for improving circulatory functions. The antagonists can be used as vasodilators, and the agonists can be used as vasoconstrictors.

The novel peptide derivatives of the present invention or the salts thereof are the endothelin antagonists having vasodilator activity or the endothelin agonists having vasopressor activity, so that they can be used as agents for improving circulatory functions or therapeutic agents for cardiac infarction, acute renal insufficiency and the like.

both of the free peptide derivatives represented by formula [I] and the alkali addition salts or the acid addition salts thereof, the dosage is generally a proper amount within the range of 1 ng to 10 mg per kg of weight, as the amount of the free derivatives.

More specifically, the dosage varies depending on the type of disease to be treated, the symptom of the disease, the object to which the drugs are given and the route of administration. For example, when given by injection to adult patients of hypertension, it is advantageous that the active ingredients (the compounds represented by formula [I]) are normally given in one dose of about 1 ng to 0.1 mg/kg of weight about once to 3 times a days. Drip infusion is also effective. In this case, the total dosage is the same as with injection.

When the peptides of the present invention are used as therapeutic agents, they must be carefully purified so as to contain no bacteria and no pyrogens.

The present invention will be described in more detail with the following Examples. The following examples are given to illustrate embodimenss of the present invention as it is presently preferred to practice. It will be understood that the examples are illustrative, and that the invention is not to be considered as restricted except as indicated in the claims. In Examples 1 to 54 and Reference Example 1, all amino acid residues other than glycine take the L-form unless otherwise specified. Table 3 shows the amino acid sequences of endothelin-1, endothelin-2, endothelin-3, mouse endothelin, known agonists and novel endothelin derivatives obtained in Examples of the present invention, compared to one another.

TABLE 3

| Known | 1 2 3 | 4 5 6 7 8 9 10 11 | 12 13 14 15 16 17 18 | 19 20 21 | | |
|---|---|---|---|---|---|---|
| ET-1 | Cys—Ser—Cys | —Ser—Ser—Leu—Met—Asp—Lys—Glu—Cys | —Val—Tyr—Phe—Cys—His—Leu—Asp | —Ile—Ile—Trp | | (SEQ ID NO: 1) |
| ET-2 | Cys—Ser—Cys | —Ser—Ser—Trp—Leu—Asp—Lys—Glu—Cys | —Val—Tyr—Phe—Cys—His—Leu—Asp | —Ile—Ile—Trp | | (SEQ ID NO: 2) |
| ET-3 | Cys—Thr—Cys | —Phe—Thr—Tyr—Lys—Asp—Lys—Glu—Cys | —Val—Tyr—Tyr—Cys—His—Leu—Asp | —Ile—Ile—Trp | | (SEQ ID NO: 3) |
| Mouse ET | Cys—Ser—Cys | —Asn—Ser—Trp—Leu—Asp—Lys—Glu—Cys | —Val—Tyr—Phe—Cys—His—Leu—Asp | —Ile—Ile—Trp | | (SEQ ID NO: 7) |
| * | Cys—Ser—Ala | —Ser—Ser—Leu—Met—Asp—Lys—Glu—Ala | —Val—Tyr—Phe—Cys—His—Leu—Asp | —Ile—Ile—Trp | | (SEQ ID NO: 8) |
| Example | Cys—A —W | —B —C —D —E —Asp—X —Glu—Y | —Val—Tyr—F —Cys—His—Leu—Z | —Ile—Ile—Trp | Abbreviation | |
| 1 | Cys—Ser—Phe | —Ser—Ser—Leu—Met—Asp—Lys—Glu—Phe | —Val—Tyr—Phe—Cys—His—Leu—Asp | —Ile—Ile—Trp | [Phe$^{3,11}$]-ET-1 | (SEQ ID NO: 9) |
| 2 | Cys—Ser—Phe | —Ser—Ser—Leu—Met—Asp—Lys—Glu—Ala | —Val—Tyr—Phe—Cys—His—Leu—Asp | —Ile—Ile—Trp | [Phe$^{3}$,Ala$^{11}$]-ET-1 | (SEQ ID NO: 10) |
| 3 | Cys—Ser—Ala | —Ser—Ser—Leu—Met—Asp—Lys—Glu—Phe | —Val—Tyr—Phe—Cys—His—Leu—Asp | —Ile—Ile—Trp | [Ala$^{3}$,Phe$^{11}$]-ET-1 | (SEQ ID NO: 11) |
| 4 | Cys—Ser—Trp | —Ser—Ser—Leu—Met—Asp—Lys—Glu—Trp | —Val—Tyr—Phe—Cys—His—Leu—Asp | —Ile—Ile—Trp | [Trp$^{3,11}$]-ET-1 | (SEQ ID NO: 12) |
| 5 | Cys—Ser—Cha | —Ser—Ser—Leu—Met—Asp—Lys—Glu—Cha | —Val—Tyr—Phe—Cys—His—Leu—Asp | —Ile—Ile—Trp | [Cha$^{3,11}$]-ET-1 | (SEQ ID NO: 13) |
| 6 | Cys—Ser—Nal(1) | —Ser—Ser—Leu—Met—Asp—Lys—Glu—Nal(1) | —Val—Tyr—Phe—Cys—His—Leu—Asp | —Ile—Ile—Trp | [Nal(1)$^{3,11}$]-ET-1 | (SEQ ID NO: 14) |
| 7 | Cys—Ser—His | —Ser—Ser—Leu—Met—Asp—Lys—Glu—His | —Val—Tyr—Phe—Cys—His—Leu—Asp | —Ile—Ile—Trp | [His$^{3,11}$]-ET-1 | (SEQ ID NO: 15) |
| 8 | Cys—Ser—Tyr | —Ser—Ser—Leu—Met—Asp—Lys—Glu—Tyr | —Val—Tyr—Phe—Cys—His—Leu—Asp | —Ile—Ile—Trp | [Tyr$^{3,11}$]-ET-1 | (SEQ ID NO: 16) |
| 9 | Cys—Ser—Thi | —Ser—Ser—Leu—Met—Asp—Lys—Glu—Thi | —Val—Tyr—Phe—Cys—His—Leu—Asp | —Ile—Ile—Trp | [Thi$^{3,11}$]-ET-1 | (SEQ ID NO: 17) |
| 10 | Cys—Ser—Phe(4F) | —Ser—Ser—Leu—Met—Asp—Lys—Glu—Phe(4F) | —Val—Tyr—Phe—Cys—His—Leu—Asp | —Ile—Ile—Trp | [Phe(4F)$^{3,11}$]-ET-1 | (SEQ ID NO: 18) |
| 11 | Cys—Ser—Phg | —Ser—Ser—Leu—Met—Asp—Lys—Glu—Phg | —Val—Tyr—Phe—Cys—His—Leu—Asp | —Ile—Ile—Trp | [Phg$^{3,11}$]-ET-1 | (SEQ ID NO: 19) |
| 12 | Cys—Ser—Tyr(Et) | —Ser—Ser—Leu—Met—Asp—Lys—Glu—Tyr(Et) | —Val—Tyr—Phe—Cys—His—Leu—Asp | —Ile—Ile—Trp | [Tyr(Et)$^{3,11}$]-ET-1 | (SEQ ID NO: 20) |
| 13 | Cys—Ser—Trp | —Ser—Ser—Leu—Met—Asp—Lys—Glu—Ala | —Val—Tyr—Phe—Cys—His—Leu—Asp | —Ile—Ile—Trp | [Trp$^{3}$,Ala$^{11}$]-ET-1 | (SEQ ID NO: 21) |
| 14 | Cys—Ser—Nal(1) | —Ser—Ser—Leu—Met—Asp—Lys—Glu—Ala | —Val—Tyr—Phe—Cys—His—Leu—Asp | —Ile—Ile—Trp | [Nal(1)$^{3}$,Ala$^{11}$]-ET-1 | (SEQ ID NO: 22) |
| 15 | Cys—Ser—Nal(2) | —Ser—Ser—Leu—Met—Asp—Lys—Glu—Ala | —Val—Tyr—Phe—Cys—His—Leu—Asp | —Ile—Ile—Trp | [Nal(2)$^{3}$,Ala$^{11}$]-ET-1 | (SEQ ID NO: 23) |
| 16 | Cys—Ser—Phg | —Ser—Ser—Leu—Met—Asp—Lys—Glu—Ala | —Val—Tyr—Phe—Cys—His—Leu—Asp | —Ile—Ile—Trp | [Phg$^{3}$,Ala$^{11}$]-ET-1 | (SEQ ID NO: 24) |
| 17 | Cys—Ser—Cha | —Ser—Ser—Leu—Met—Asp—Lys—Glu—Ala | —Val—Tyr—Phe—Cys—His—Leu—Asp | —Ile—Ile—Trp | [Cha$^{3}$,Ala$^{11}$]-ET-1 | (SEQ ID NO: 25) |
| 18 | Cys—Ser—Thi | —Ser—Ser—Leu—Met—Asp—Lys—Glu—Ala | —Val—Tyr—Phe—Cys—His—Leu—Asp | —Ile—Ile—Trp | [Thi$^{3}$,Ala$^{11}$]-ET-1 | (SEQ ID NO: 26) |
| 19 | Cys—Ser—Tyr(Et) | —Ser—Ser—Leu—Met—Asp—Lys—Glu—Ala | —Val—Tyr—Phe—Cys—His—Leu—Asp | —Ile—Ile—Trp | [Tyr(Et)$^{3}$,Ala$^{11}$]-ET-1 | (SEQ ID NO: 27) |
| 20 | Cys—Ser—Phe(4F) | —Ser—Ser—Leu—Met—Asp—Lys—Glu—Ala | —Val—Tyr—Phe—Cys—His—Leu—Asp | —Ile—Ile—Trp | [Phe(4F)$^{3}$,Ala$^{11}$]-ET-1 | (SEQ ID NO: 28) |
| 21 | Cys—Ser—Ala | —Ser—Ser—Leu—Met—Asp—Lys—Glu—Ala | —Val—Tyr—Phe—Cys—His—Leu—Ala | —Ile—Ile—Trp | [Ala$^{3,11,18}$]-ET-1 | (SEQ ID NO: 29) |
| 22 | Cys—Ser—Ala | —Ser—Ser—Leu—Met—Asp—Lys—Glu—Ala | —Val—Tyr—Phe—Cys—His—Leu—Leu | —Ile—Ile—Trp | [Ala$^{3,11}$,Leu$^{18}$]-ET-1 | (SEQ ID NO: 30) |
| 23 | Cys—Ser—Ala | —Ser—Ser—Leu—Met—Asp—Lys—Glu—Ala | —Val—Tyr—Phe—Cys—His—Leu—Phe | —Ile—Ile—Trp | [Ala$^{3,11}$,Phe$^{18}$]-ET-1 | (SEQ ID NO: 31) |
| 24 | Cys—Ser—Ala | —Ser—Ser—Leu—Met—Asp—Lys—Glu—Ala | —Val—Tyr—Phe—Cys—His—Leu—Gly | —Ile—Ile—Trp | [Ala$^{3,11}$,Gly$^{18}$]-ET-1 | (SEQ ID NO: 32) |
| 25 | Cys—Ser—Cys | —Ser—Ser—Leu—Met—Asp—Lys—Glu—Cys | —Val—Tyr—Phe—Cys—His—Leu—Ala | —Ile—Ile—Trp | [Ala$^{18}$]-ET-1 | (SEQ ID NO: 33) |
| 26 | Cys—Ser—Cys | —Ser—Ser—Leu—Met—Asp—Lys—Glu—Cys | —Val—Tyr—Phe—Cys—His—Leu—Leu | —Ile—Ile—Trp | [Leu$^{18}$]-ET-1 | (SEQ ID NO: 34) |
| 27 | Cys—Ser—Cys | —Ser—Ser—Leu—Met—Asp—Lys—Glu—Cys | —Val—Tyr—Phe—Cys—His—Leu—Val | —Ile—Ile—Trp | [Val$^{18}$]-ET-1 | (SEQ ID NO: 35) |
| 28 | Cys—Ser—Cys | —Ser—Ser—Leu—Met—Asp—Lys—Glu—Cys | —Val—Tyr—Phe—Cys—His—Leu—Gly | —Ile—Ile—Trp | [Gly$^{18}$]-ET-1 | (SEQ ID NO: 36) |
| 29 | Cys—Ser—Cys | —Ser—Ser—Leu—Met—Asp—Lys—Glu—Cys | —Val—Tyr—Phe—Cys—His—Leu—D-Ala | —Ile—Ile—Trp | [D-Ala$^{18}$]-ET-1 | |
| 30 | Cys—Ser—Cys | —Ser—Ser—Leu—Met—Asp—Lys—Glu—Cys | —Val—Tyr—Phe—Cys—His—Leu—Abu | —Ile—Ile—Trp | [Abu$^{18}$]-ET-1 | (SEQ ID NO: 37) |
| 31 | Cys—Ser—Cys | —Ser—Ser—Leu—Met—Asp—Lys—Glu—Cys | —Val—Tyr—Phe—Cys—His—Leu—Nva | —Ile—Ile—Trp | [Nva$^{18}$]-ET-1 | (SEQ ID NO: 38) |
| 32 | Cys—Ser—Cys | —Ser—Ser—Leu—Met—Asp—Lys—Glu—Cys | —Val—Tyr—Phe—Cys—His—Leu—Nle | —Ile—Ile—Trp | [Nle$^{18}$]-ET-1 | (SEQ ID NO: 39) |
| 33 | Cys—Ser—Cys | —Ser—Ser—Leu—Met—Asp—Lys—Glu—Cys | —Val—Tyr—Phe—Cys—His—Leu—Phe | —Ile—Ile—Trp | [Phe$^{18}$]-ET-1 | (SEQ ID NO: 40) |
| 34 | Cys—Ser—Cys | —Ser—Ser—Leu—Met—Asp—Lys—Glu—Cys | —Val—Tyr—Phe—Cys—His—Leu—Ser | —Ile—Ile—Trp | [Ser$^{18}$]-ET-1 | (SEQ ID NO: 41) |
| 35 | Cys—Ser—Cys | —Ser—Ser—Trp—Leu—Asp—Lys—Glu—Cys | —Val—Tyr—Phe—Cys—His—Leu—Asn | —Ile—Ile—Trp | [Asn$^{18}$]-ET-1 | (SEQ ID NO: 42) |
| 36 | Cys—Ser—Cys | —Ser—Ser—Trp—Leu—Asp—Lys—Glu—Cys | —Val—Tyr—Phe—Cys—His—Leu—Ala | —Ile—Ile—Trp | [Ala$^{18}$]-ET-1 | (SEQ ID NO: 43) |
| 37 | Cys—Thr—Cys | —Phe—Thr—Tyr—Lys—Asp—Lys—Glu—Cys | —Val—Tyr—Tyr—Cys—His—Leu—Ala | —Ile—Ile—Trp | [Ala$^{18}$]-ET-1 | (SEQ ID NO: 44) |
| 38 | Cys—Ser—Leu | —Ser—Ser—Leu—Met—Asp—Lys—Glu—Leu | —Val—Tyr—Phe—Cys—His—Leu—Asp | —Ile—Ile—Trp | [Leu$^{3,11}$]-ET-1 | (SEQ ID NO: 45) |
| 39 | Cys—Ser—Val | —Ser—Ser—Leu—Met—Asp—Lys—Glu—Val | —Val—Tyr—Phe—Cys—His—Leu—Asp | —Ile—Ile—Trp | [Val$^{3,14}$]-ET-1 | (SEQ ID NO: 46) |
| 40 | Cys—Ser—Met | —Ser—Ser—Leu—Met—Asp—Lys—Glu—Met | —Val—Tyr—Phe—Cys—His—Leu—Asp | —Ile—Ile—Trp | [Met$^{3,11}$]-ET-1 | (SEQ ID NO: 47) |
| 41 | Cys—Ser—Ser | —Ser—Ser—Leu—Met—Asp—Lys—Glu—Ala | —Val—Tyr—Phe—Cys—His—Leu—Asp | —Ile—Ile—Trp | [Val$^{3}$,Ala$^{11}$]-ET-1 | (SEQ ID NO: 48) |
| 42 | Cys—Ser—Val | —Ser—Ser—Leu—Met—Asp—Lys—Glu—Ser | —Val—Tyr—Phe—Cys—His—Leu—Asp | —Ile—Ile—Trp | [Ser$^{3,11}$]-ET-1 | (SEQ ID NO: 49) |
| 43 | Cys—Ser—Cys | —Ser—Ser—Leu—Met—Asp—Lys—Glu—Cys | —Val—Tyr—Phe—Cys—His—Leu—Ile | —Ile—Ile—Trp | [Ile$^{18}$]-ET-1 | (SEQ ID NO: 50) |
| 44 | Cys—Ser—Cys | —Ser—Ser—Leu—Met—Asp—Lys—Glu—Cys | —Val—Tyr—Phe—Cys—His—Leu—t-Leu | —Ile—Ile—Trp | [t-Leu$^{18}$]-ET-1 | (SEQ ID NO: 51) |
| 45 | Cys—Ser—Cys | —Ser—Ser—Leu—Met—Asp—Lys—Glu—Cys | —Val—Tyr—Phe—Cys—His—Leu—$\tau$-Leu | —Ile—Ile—Trp | [$\tau$-Leu $^{18}$]-ET-1 | (SEQ ID NO: 52) |

TABLE 3-continued

| | | | | | | |
|---|---|---|---|---|---|---|
| 46 | Cys—Ser—Cys | —Ser—Ser—Leu—Met—Asp—Lys—Glu—Cys | —Val—Tyr—Phe—Cys—His—Leu—Glu | —Ile—Ile—Trp | [$Glu^{18}$]-ET-1 | (SEQ ID NO: 53) |
| 47 | Cys—Ser—Cys | —Ser—Ser—Leu—Met—Asp—Lys—Glu—Cys | —Val—Tyr—Phe—Cys—His—Leu—Lys | —Ile—Ile—Trp | [$Lys^{18}$]-ET-1 | (SEQ ID NO: 54) |
| 48 | Cys—Ser—Cys | —Ser—Ser—Leu—Met—Asp—Leu—Glu—Cys | —Val—Tyr—Phe—Cys—His—Leu—Leu | —Ile—Ile—Trp | [$Leu^{9,18}$]-ET-1 | (SEQ ID NO: 55) |
| 49 | Cys—Ser—Cys | —Ser—Ser—Trp—Leu—Asp—Lys—Glu—Cys | —Val—Tyr—Phe—Cys—His—Leu—Ile | —Ile—Ile—Trp | [$Ile^{18}$]-ET-1 | (SEQ ID NO: 56) |
| 50 | Cys—Thr—Cys | —Phe—Thr—Tyr—Lys—Asp—Lys—Glu—Cys | —Val—Tyr—Tyr—Cys—His—Leu—Ile | —Ile—Ile—Trp | [$Ile^{18}$]-ET-1 | (SEQ ID NO: 57) |
| 51 | Cys—Ser—Cys | —Ser—Ser—Leu—Met—Asp—Lys—Glu—Cys | —Val—Tyr—Phe—Cys—His—Leu—Thr | —Ile—Ile—Trp | [$Thr^{18}$]-ET-1 | (SEQ ID NO: 58) |
| 52 | Cys—Ser—Leu | —Ser—Ser—Leu—Met—Asp—Lys—Glu—Ala | —Val—Tyr—Phe—Cys—His—Leu—Asp | —Ile—Ile—Trp | [$Leu^{3}$,$Ala^{11}$]-ET-1 | (SEQ ID NO: 59) |
| 53 | Cys—Ser—Nal(2) | —Ser—Ser—Leu—Met—Asp—Lys—Glu—Nal(2) | —Val—Tyr—Phe—Cys—His—Leu—Asp | —Ile—Ile—Trp | [$Nal(2)^{3,11}$]-ET-1 | (SEQ ID NO: 60) |
| 54 | Cys—Ser—Cys | —Ser—Ser—Leu—Met—Asp—Lys—Glu—Cys | —Val—Tyr—Phe—Cys—His—Leu—Met | —Ile—Ile—Trp | [$Met^{18}$]-ET-1 | (SEQ ID NO: 61) |
| Rf. 1 | Cys—Ser—Ala | —Ser—Ser—Leu—Met—Asp—Lys—Glu—Ala | —Val—Tyr—Phe—Cys—Leu—Asp | —Ile—Ile—Trp | [$Ala^{3,11}$,$deHis^{18}$]-ET-1 | (SEQ ID NO: 62) |

[* J. Cardiovascular Pharmacology, 13 S197 (1989)]

Note:

$Cys^{1}$ and $Cys^{15}$ of the above compounds form an S—S bond, and in the compounds having $Cys^{3}$ and $Cys^{11}$, $Cys^{3}$ and $Cys^{11}$ also form an S—S bond.

EXAMPLE 1 PRODUCTION OF [Phe$^{3,11}$]-ET-1 (SEQ ID NO:9)

A Boc-Trp(For)-OCH2-Pam resin (0.5 mmole) was used as a starting material, and Boc-amino acid derivative cartridges (2.0 mmoles) (Applied Biosystems). After elimination of the Boc groups with trifluoroacetic acid, a peptide chain was successively extended from the C-terminal side by the HOBt active ester method. Boc-Asp(OcHex) and Boc-Glu(OcHex) were used after the powders manufactured by Peptide Laboratory were enclosed in cartridges. In this manner, the protected peptide resin represented by the following formula was obtained:

Boc-Cys(MeBzl)-Ser(Bzl)-Phe-Ser(Bzl)-Ser(Bzl)-Leu-Met-Asp(OcHex)-Lys(ClZ)-Glu(OcHex)-Phe-Val-Tyr(BrZ)-Phe-Cys(MeBzl)-His(Dnp)-Leu-Asp(OcHex)-Ile-Ile-Trp(For)-OCH$_2$-Pam resin.

This peptide resin was suspended in 10 ml of DMF, and 1.0 ml of thiophenol was added thereto. The Dnp group, a protective group for the imidazole ring of His, was eliminated by stirring at room temperature for 2 hours, and the Boc groujp was further eliminated by treating with 50% TFA/dichloromethane containing 0.1% indole at room temperature for 20 minites. 500 mg of the peptide resin thus obtained was treated with 5 ml of anhydrous hydrogen fluoride in the presence of 500 mg of p-cresol and 0.75 ml of 1,4-butanediol at 0° C. for 1 hour to remove all of the protective groups and to cut off the peptide from the resin. Hydrogen fluoride was removed by distillation, and ethyl ether was added to the residue to deposit a precipitate. The precipitate was filtered off, and 30 ml of TFA was added thereto to dissolve it. The resin was removed by filtration, and the filtrate was concentrated. Ethyl ether was added to the residue to deposit a precipitate. The precipitate was filtered off, and dried under reduced pressure. The resulting product was dissolved in 1 l of a 0.1 M aqueous solution of ammonium acetate (pH 8.0), and oxidized with air by stirring at room temperature for 10 hours. Then, acetic acid was added thereto to adjust the solution to pH 5.0, followed by lyophilization. The lyophilized product was dissolved in 20 ml of 60% acetic acid. The resulting solution was subjected to a Sephadex G-50 column (5 cm×108 cm) and eluted with 60% acetic acid. The desired fractions were collected and lyophilized. Finally, the fractions were purified by high performance liquid chromatography using a YMC-D-ODS-5 column (2 cm×25 CM, Yamamura Chemical) to obtain the desired product.

Anal. for amino acids (hydrolysis at 110° C. for 24 hours; numerals in parentheses indicate theoretical values): Asp 2.00(2); Ser 2.59(3); Glu 1.06(1); Cyt 0.34(1); Val 0.93(1); Met 0.99(1); Ile 1.08(2); Leu 2.01(2); Tyr 0.89(1); Phe 2.98(3); Lys 1.02(1); His 0.97(1)

LSIMS (M +H+) =2581 (theoretical value =2581).

EXAMPLE 2 PRODUCTION OF [Phe$^3$, Ala$^{11}$]-ET-1 (SEQ ID NO:10)

The following protected peptide resin was obtained by procedures similar to those of Example 1:

Boc-Cys(MeBzl)-Ser(Bzl)-Phe-Ser(Bzl)-Ser(Bzl)-Leu-Met-Asp(OcHex)-Lys(Clz)-Glu(OcHex)-Ala-Val-Tyr(BrZ)-Phe-Cys(MeBzl)-His(Dnp)-Leu-Asp(OcHex)-Ile-Ile-Trp(Fkor)-O-CH$_2$-Pam resin.

The resulting peptide resin was further deprotected, oxidized and purified as with Example 1 to obtain the desired product.

Anal. for amino acids: Asp 2.00(2); Ser 2.62(3); Glu 1.05(1); Ala 1.01(1); Cyt 0.46(1); Val 0.95(1); Met 0.96(1); Ile 1.09(2); Leu 2.01(2); Tyr 0.87(1); Phe 1.99(2); Lys 1.02(1); His 0.97(1).

LSIMS (M +H ) =2505 (theoretical value=2505).

EXAMPLE 3 PRODUCTION OF [Ala$^3$, Phe$^{11}$]-ET-1 (SEQ ID NO:11)

The following protected peptide resin was obtained by procedures similar to those of Example 1:

Boc-Cys(MeBzl)-Ser(Bzl)-Ala-Ser(Bzl)-Ser(Bzl)-Leu-Met-Asp(OcHex)-Lys(ClZ)-Glu(OcHex)-Phe-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.66(3); Glu 1.06(1); Ala 1.01(1); Cyt 0.46(1); Val 0.96(1); Met 0.99(1); Ile 1.10(2); Leu 1.99(2); Tyr 0.88(1); Phe 1.97(2); Lys 1.02(1); His 0.97(1).

LSIMS (M+H+)=2505 (theoretical value =2505).

EXAMPLE 4 PRODUCTION OF [Trp$^{3,11}$]-ET-1

The following protected peptide resin was obtained by procedures similar to those of Example 1:

Boc-Cys(MeBzl)-Ser(Bzl)-Trp(For)-Ser(Bzl)-Ser(Bzl)-Leu-Met-Asp(OcHex)-Lys(ClZ)-Glu(OcHex)-Trp(For)-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.61(3); Glu 1.04(1); Cyt 0.42(1); Val 0.96(1); Met 0.97(1); Ile 1.07(2); Leu 2.00(2); Tyr 0.89(1); Phe 1.01(1); Lys 1.02(1); His 0.97(1).

LSIMS (M+H+)=2659 (theoretical value=2659,).

EXAMPLE 5 PRODUCTION OF l[Cha$^{3,11}$]-ET-1 (SEQ ID NO:13)

The following protected peptide resin was obtained by procedures similar to those of Example 1 except that Boc-Cha (Nova) was used:

Boc-Cys(MeBzl)-Ser(Bzl)-Cha-Ser(Bzl)-Ser(Bzl)-Leu-Met-Asp(OcHex)-Lys(ClZ)-Glu(OcHex)-Cha-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.63(3); Glu 1.04(1); Cyt 0.46(1); Val 0.94(1); Met 0.97(1); Ile 1.06(2); Leu 2.01(2); Tyr 0.88(1); Phe 1.01(1); Lys 1.02(1); His 0.98(1).

LSIMS (M+H+)=2593 (theoretical value=2593).

EXAMPLE 6 PRODUCTION OF [Nal(l)$^{3,11}$]-ET-1 (SEQ ID NO:14)

The following protected peptide resin was obtained by procedures similar to those of Example 1 except that Boc-Nal(1) prepared by protecting Nal(1) (BACHEM) with a Boc group using (Boc)$_2$O was used:

Boc-Cys(MeBzl)-Ser(Bzl)-Nal(1)-Ser(Bzl)-Ser(Bzl)-Leu-Met-Asp(OcHex)-Lys(ClZ)-Glu(OcHex)-Nal(1)-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.58(3); Glu 1.03(1); Cyt 0.39(1); Val 0.94(1); Met 0.98(1); Ile 1.05(2); Leu 2.00(2); Tyr 0.92(1); Phe 1.01(1); Lys 1.02(1); His 0.98(1).

LSIMS $(M+H^+) = 2681$ (theoretical value = 2681)

EXAMPLE 7 PRODUCTION OF [His$^{3,11}$]-ET-1 (SEQ ID NO:15)

The following protected peptide resin was obtained by procedures similar to those of Example 1:

Boc-Cys(MeBzl)-Ser(Bzl)-His(Dnp)-Ser(Bzl)-Ser(Bzl)-Leu-Met-Asp(OcHex)-Lys(ClZ)-Glu(OcHex)-His(Dnp)-Val-Tyr(BrZ)-Phe-Cys(MeBzl)-His(Dnp)-Leu-Asp(OcHex)-Ile-Ile-Trp(For)-O-CH2-Pam resin.

The resulting peptide resin was further deprotected, oxidized and purified as with Example 1 to obtain the desired product.

Anal. for amino acids: Asp 2.00(2); Ser 2.62(3); Glu 1.05(1); Cyt 0.41(1); Val 0.96(1); Met 0.97(1); Ile 1.08(2); Leu 2.01(2); Tyr 0.89(1); Phe 1.00(1); Lys 1.01(1); His 2.89(3)

LSIMS $(M+H^+) = 2659$ (theoretical value = 2659).

EXAMPLE 8 PRODUCTION OF [Tyr$^{3,11}$]-ET-1 (SEQ ID NO:16)

The following protected peptide resin was obtained by procedures similar to those of Example 1:

Boc-Cys(MeBzl)-Ser(Bzl)-Tyr(BrZ)-Ser(Bzl)-Ser(Bzl)-Leu-Met-Asp(OcHex)-Lys(ClZ)-Glu(OcHex)-Tyr(Brz)-Val-Tyr(BrZ)-Phe-Cys(MeBzl)-His(Dnp)-Leu-Asp(OcHex)-Ile-Ile-Trp(For)-O-CH2-Pam resin.

The resulting peptide resin was further deprotected, oxidized and purified as with Example 1 to obtain the desired product.

Anal. for amino acids: Asp 2.00(2); Ser 2.61(3); Glu 1.03(1); Cyt 0.42(1); Val 0.94(1); Met 0.97(1); Ile 1.09(2); Leu 2.01(2);Tyr 2.69(3); Phe 1.02(1); Lys 1.02(1); His 0.98(1)

LSIMS $(M+H^+) = 2613$ (theoretical value = 2613).

EXAMPLE 9 PRODUCTION OF [The$^{3,11}$]-ET-1 (SEQ, ID NO: 17)

The following protected peptide resin was obtained by procedures similar to those of Example 1:

Boc-Cys(MeBzl)-Ser(Bzl)-Thi-Ser(Bzl)-Ser(Bzl)-Leu-Met-Asp(OcHex)-Lys(ClZ)-Glu(OcHex)-Thi-Val-Tyr(BrZ)-Phe-Cys(MeBzl)-His(Dnp)-Leu-Asp(OcHex)-Ile-Ile-Trp(For)-O-CH2-Pam resin The resulting peptide resin was further deprotected, oxidized and purified as with Example 1 to obtain the desired product.

Anal. for amino acids: Asp 2.00(2); Ser 2.62(3); Glu 1.07(1); Cyt 0.41(1); Val 0.95(1); Met 0.98(1); Ile 1.07(2); Leu 2.01(2); Tyr 0.90(1); Phe 1.01(1); Lys 1.02(1); His 0.97(1).

LSIMS $(M+H^+) = 2593$ (theoretical value = 2593) .

EXAMPLE 10 PRODUCTION OF [Phe(4F)$^{3,11}$]-ET-1 (SEQ ID NO:18)

The following protected peptide resin was obtained by procedures similar to those of Example 1 except that Boc-Phe(4F) prepared by protecting Phe(4F) (Nova) with a Boc group using (Boc)2O was used:

Boc-Cys(MeBzl)-Ser(Bzl)-Phe(4F)-Ser(Bzl)-Ser(Bzl)-Leu-Met-Asp(OcHex)-Lys(ClZ)-Glu(OcHex)-Phe(4F)-Val-Tyr(BrZ)-Phe-Cys(MeBzl)-His(Dnp)-Leu-Asp(OcHex)-Ile-Ile-Trp(For)-O-CH2-Pam resin The resulting peptide resin was further deprotected, oxidized and purified as with Example 1 to obtain the desired product.

Anal for amino acids: Asp 2.00(2); Ser 2.63(3); Glu 1.06(1); Cyt 0.45(1); Val 0.94(1); Met 0.96(1); Ile 1.11(2); Leu 2.03(2); Tyr 0.91(1); Phe 1.01(1); Lys 1.02(1); His 0.98(1)

LSIMS $(M+H^+) = 2681$ (theoretical value = 2681).

EXAMPLE 11 PRODUCTION OF [Phg$^{3,11}$[-ET-1 (SEQ ID NO: 19)

The following protected peptide resin was obtained by procedures similar to those of Example 1 except that Boc-Phg (Nova) was used:

Boc-Cys(MeBzl)-Ser(Bzl)-Phg-Ser(Bzl)-Ser(Bzl)-Leu-Met-Asp(OcHex)-Lys(ClZ)-Glu(OcHex)-Phg-Val-Tyr(Brz)-Phe-Cys(MeBzl)-His-(Dnp)-Leu-Asp(OcHex)-Ile-Ile-Trp(For)-O-CH2-Pam resin.

The resulting peptide resin was further deprotected, oxidized and purified as with Example 1 to obtain the desired product.

Anal. for amino acids: Asp 2.00(2); Ser 2.65(3); Glu 1.08(1); Cyt 0.43(1); Val 0.94(1); Met 0.97(1); Ile 1.09(2); Leu 2.00(2); Tyr 0.88(1); Phe 1.01(1); Lys 1.02(1); His 0.98(1).

LSIMS $(M+H^+) = 2553$ (theoretical value = 2553).

EXAMPLE 12 PRODUCTION OF [Tyr(Et)$^{3,11}$]-ET-1 (SEQ ID NO:20)

The following protected peptide resin was obtained by procedures similar to those of Example 1 except that Boc-Tyr(Et) (Nova) was used:

Boc-Cys(MeBzl)-Ser(Bzl)-Tyr(Et)-Ser(Bzl-Ser(Bzl)-Leu-Met-Asp(OcHex)-Lys(ClZ)-Glu(OcHex)-Tyr-Et)-Val-Tyr(BrZ)-Phe-Cys(MeBzl)-His(Dnp)-Leu-Asp(OcHex)-Ile-Ile-Trp(For)-O-CH2-Pam resin.

The resulting peptide resin was further deprotected, oxidized and purified as with Example 1 to obtain the desired product.

Anal. for amino acids: Asp 2.00(2); Ser 2.58(3); Glu 1.08(1); Cyt 0.42(1); Val 0.94(1); Met 0.96(1); Ile 1.09(2); Leu 2.02(2); Tyr 2.52(3); Phe 1.02(1); Lys 1.02(1); His 0.98(1)

LSIMS $(M+H^+) = 2669$ (theoretical value = 2669)

EXAMPLE 13 PRODUCTION OF [Trp$^3$, Ala$^{11}$]-ET-1 (SEQ ID NO:21)

The following protected peptide resin was obtained by procedures similar to those of Example 1:

Boc-Cys(MeBzl)-Ser(Bzl)-Trp(For)-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Asp(OcHex)-Ile-Ile-Trp(For)-O-CH2-Pam resin.

The resulting peptide resin was further deprotected, oxidized and purified as with Example 1 to obtain the desired product.

Anal. for amino acids: Asp 2.00(2); Ser 2.56(3); Glu 1.07(1); Ala 1.01(1); Cyt 0.45(1); Val 0.94(1); Met 0.97(1); Ile 1.09(2); Leu 2.01(2); Tyr 0.88(1); Phe 1.01(1); Lys 1.02(1); His 0.97(1).

LSIMS $(M+H^+) = 2544$ (theoretical value = 2544).

EXAMPLE 14 PRODUCTION OF [Nal(1)³, Ala¹¹]-ET-1 (SEQ ID NO:22).

The following protected peptide resin was obtained by procedures similar to those of Example 1:
Boc-Cys(MeBzl)-Ser(Bzl)-Nal(1)-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Asp(OcHex)-Ile-Ile-Trp(For)-O-CH₂-Pam resin.

The resulting peptide resin was further deprotected, oxidized and purified as with Example 1 to obtain the desired product.

Anal. for amino acids: Asp 2.00(2); Ser 2.61(3); Glu 1.06(1); Ala 1.01(1); Cyt 0.43(1); Val 0.96(1); Met 0.95(1); Ile 1.09(2); Leu 2.01(2); Tyr 0.89(1); Phe 0.99(1); Lys 1.01(1); His 0.96(1)

LSIMS (M+H+)=2555 (theoretical value=2555).

EXAMPLE 15 PRODUCTION OF [Nal(2)³, Ala¹¹]-ET-1 (SEQ ID NO:23)

The following protected peptide resin was obtained by procedures similar to those of Example 1 except that Boc-Nal(2) prepared by protecting Nal(2) (BACHEM) with a Boc group using (Boc)₂O was used:
Boc-Cys(MeBzl)-Ser(Bzl)-Nal(2)-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Asp(OcHex)-Ile-Ile-Trp(For)-O-CH₂-Pam resin.

The resulting peptide resin was further deprotected, oxidized and purified as with Example 1 to obtain the desired product.

Anal. for amino acids: Asp 2.00(2); Ser 2.60(3); Glu 1.07(1); Ala 1.01(1); Cyt 0.42(1); Val 0.96(1); Met 0.95(1); Ile 1.10(2); Leu 2.01(2); Tyr 0.89(1); Phe 1.00(1); Lys 1.02(1); His 0.97(1).

LSIMS (M+H+)=2555 (theoretical value=2555).

EXAMPLE 16 PRODUCTION OF [Phg³, Ala¹¹]-ET-1 (SQ ID NO:24)

The following protected peptide resin was obtained by procedures similar to those of Example 1:
Boc-Cys(MeBzl)-Ser(Bzl)-Phg-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Asp(OcHex)-Ile-Ile-Trp(For)-O-CH₂-Pam resin.

The resulting peptide resin was further deprotected, oxidized and purified as with Example 1 to obtain the desired product.

Anal. for amino acids: Asp 2.00(2); Ser 2.65(3); Glu 1.08(1); Ala 1.02(1); Cyt 0.41(1); Val 0.94(1); Met 0.96(1); Ile 1.08(2); Leu 2.02(2); Tyr 0.88(1); Phe 1.01(1); Lys 1.02(1); His 0.97(1).

LSIMS (M+H+)=2492 (theoretical value=2491).

EXAMPLE 17 PRODUCTION OF [Cha³, Ala¹¹]-ET-1 (SEQ ID NO:25)

The following protected peptide resin was obtained by procedures similar to those of Example 1:
Boc-Cys(MeBzl)-Ser(Bzl)-Cha-Ser(Bzl)-Ser(Bzl)-Leu-Met-Asp(OcHex)-Lys(ClZ)-Glu(OcHex)-Ala-Val-Tyr(BrI)-Phe-Cys(MeBzl)-His(Dnp)-Leu-Asp(OcHex)-Ile-Ile-Trp(For)-O-CH₂-Pam resin.

The resulting peptide resin was further deprotected, oxidized and purified as with Example 1 to obtain the desired product.

Anal. for amino acids: Asp 2.00(2); Ser 2.58(3); Glu 1.06(1); Ala 1.01(1); Cyt 0.39(1); Val 0.94(1); Met 0.97(1); Ile 1.08(2); Leu 2.03(2); Tyr 0.87(1); Phe 1.01(1); Lys 1.02(1); His 0.98(1).

LSIMS (M+H+)=2511 (theoretical value=2511).

EXAMPLE 18 PRODUCTION OF [Thi³, Ala¹¹]-ET-1 (SEQ ID NO:26)

The following protected peptide resin was obtained by procedures similar to those of Example 1:
Boc-Cys(MeBzl)-Ser(Bzl)-Thi-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Asp(OcHex)-Ile-Ile-Trp(For)-O-CH₂ Pam resin.

The resulting peptide resin was further deprotected, oxidized and purified as with Example 1 to obtain the desired product.

Anal. for amino acids: Asp 2.00(2); Ser 2.59(3); Glu 1.07(1); Ala 1.01(1); Cyt 0.41(1); Val 0.95(1); Met 0.97(1); Ile 1.08(2); Leu 2.02(2); Tyr 0.87(1); Phe 1.00(1); Lys 1.02(1); His 0.98(1).

LSIMS (M+H+)=2511 (theoretical value=2511).

EXAMPLE 19 PRODUCTION OF [Try(Et)³. Ala¹¹]-ET-1 (SEQ ID NO:27)

The following protected peptide resin was obtained by procedures similar to those of Example 1:
BocCCys(MeBzl)-Ser(Bzl)-Tkyr(Et)-Ser(Bzl)-Ser(Bzl)-Leu-Met-Asp(OcHex)-Lys(ClZ)-Glu(OcHex)-Ala-Val-Tyr(BrZ)-Phe-Cys(MeBzL)-His(Dnp)-Leu-Asp(OcHex)-Ile-le-Trp(For)-O-CH₂-Pam resin.

The resulting peptide resin was further deprotected, oxidized and purified as with Example 1 to obtain the desired product.

Anal. for amino acids: Asp 2.00(2); Ser 2.57(3); Glu 1:06(1); Ala 1.00(1); Cyt 0.43(1); Val 0.93(1); Met 0.97(1); Ile 1.11(2); Leu 2.02(2); Tyr 1.70(1); Phe 1.00(1); Lys 1.02(1); His 0.97(1).

LSIMS (M+H+)=2549 (theoretical value=2549).

EXAMPLE 20 PRODUCTION OF [Phe(4F)³, Ala¹¹]-ET-1 (SEQ ID NO:28)

The following protected peptide resin was obtained by procedures similar to those of Example 1:
Boc-Cys(MeBzl)-Ser(Bzl)-Phe(4F)-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Lu-Asp(OcHex)-Ile-Ile-Trp(For)-O-CH₂-Pam resin.

The resulting peptide resin was further deprotected, oxidized and purified as with Example 1 to obtain the desired product.

Anal. for amino acids: Asp 2.00(2); Ser 2.63(3); Glu 1.06(1); Ala 1.02(1); Cyt 0.43(1); Val 0.97(1); Met 0.98(1); Ile 1.12(2); Leu 2.01(2); Tyr 0.89(1); Phe 1.01(1); Lys 1.02(1); His 0.97(1).

LSIMS (M+H+)=2523 (theoretical value=2523).

EXAMPLE 21 PRODUCTION OF [Ala³,¹¹,¹⁸]-ET-1 (SEQ ID NO:29)

The following protected peptide resin was obtained by procedures similar to those of Example 1:
Boc-Cys(MeBzl)-Ser(Bzl)-Ala-Ser(Bzl)-Ser(Bzl)-Leu-Met- Asp(OcHex)-Lys(ClZ)-Glu(OcHex)-Ala-Val-Tyr(BrZ)-Phe-Cys(MeBzl)-His(Dnp)-Leu-Ala-Ile-Ile-Trp(For)-O-CH₂Pam resin.

The resulting peptide resin was further deprotected, oxidized and purified as with Example 1 to obtain the desired product.

Anal. for amino acids: Asp 1.03(1); Ser 2.67(3); Glu 1.07(1); Ala 3.00(3); Cyt 0.71(1); Val 0.91(1); Met 1.00(1); Ile 1.04(2); Leu 2.09(2); Tyr 0.92(1); Phe 1.04(1); Lys 1.08(1); His 0.99(1).

LSIMS (M+H+) = 2385 (theoretical value = 2385)

EXAMPLE 22 PRODUCTION OF [Ala$^{3,11}$, Leu$^{18}$]-ET-1 (SEQ ID NO:30)

The following protected peptide resin was obtained by procedures similar to those of Example 1:

Boc-Cys(MeBzl)-Ser(Bzl)-Ala-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Leu-Ile-Ile-Trp(For)-O-CH$_2$-Pam resin.

The resulting peptide resin was further deprotected, oxidized and purified as with Example 1 to obtain the desired product.

Anal. for amino acids: Asp 1.03(1); Ser 2.71(3); Glu 1.10(1); Ala 2.00(2); Cyt 0.82(1); Val 0.95(1); Met 0.99(1); Ile 0.78(2); Leu 2.66(3); Tyr 0.92(1); Phe 1.02(1); Lys 1.07(1); His 0.84(1).

LSIMS (M+H+) = 2427 (theoretical value = 2427).

EXAMPLE 23 PRODUCTION OF [Ala$^{3,11}$, Phe$^{18}$]-ET-1 (SEQ ID NO:31)

The following protected peptide resin was obtained by procedures similar to those of Example 1:

Boc-Cys(MeBzl)-Ser(Bzl)-Ala-Ser(Bzl)-Ser(Bzl)-Leu-Met-Asp(OcHex)-Lyz(ClZ)-Glu(OcHex)-Ala-Val-Tyr(BrZ)-Phe-Cys(MeBzl)-His(Dnp)-Leu-Phe-Ile-Ile-Trp(For)-O-CH$_2$-Pam resin.

The resulting peptide resin was further deprotected, oxidized and purified as with Example 1 to obtain the desired product.

Anal. for amino acids: Asp 0.99(1); Ser 2.56(3); Glu 1.04(1); Ala 2.00(2); Cyt 0.33(1); Val 0.88(1); Met 0.98(1); Ile 1.13(2); Leu 2.01(2); Tyr 0.84(1); Phe 1.96(2); Lys 1.04(1); His 0.97(1).

LSIMS (M+H+) = 2461 (theoretical value = 2461).

EXAMPLE 24 PRODUCTION OF [Ala$^{3,11}$, Gly$^{18}$[-ET-1 (SEQ ID NO:32)

The following protected peptide resin was obtained by procedures similar to those of Example 1:

Boc-Cys(MeBzl)-Ser(Bzl)-Ala-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Gly-Ile-Ile-Trp(For)-O-CH$_2$-Pam resin.

The resulting peptide resin was further deprotected, oxidized and purified as with Example 1 to obtain the desired product.

Anal. for amino acids: Asp 1.04(1); Ser 2.66(3); Glu 1.06(1); Gly 1.01(1); Ala 2.00(2); Cyt 0.45(1); Val 0.91(1); Met 1.01(1); Ile 1.06(2); Leu 2.07(2); Tyr 0.91(1); Phe 1.03(1); Lys 1.06(1); His 0.98(1).

LSIMS (M+H+) = 2371 (theoretical value = 2371).

EXAMPLE 25 PRODUCTION OF [Ala$^{18}$]-ET-1 (SEQ ID NO:33)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Ala-Ile-Ile-Trp(For)-O-CH$_2$-Pam resin.

The resulting peptide resin was further deprotected, oxidized and purified as with Example 1 to obtain the desired product.

Anal. for amino acids: Asp 1.02(1); Ser 2.65(3); Glu 1.07(1); Ala 1.00(1); Cyt 0.95(2); Val 0.95(1); Met 0.99(1); Ile 1.07(2); Leu 2.07(1); Tyr 0.91(1); Phe 1.03(1); Lys 1.05(1); His 0.98(1).

LSIMS (M+H+) = 2447 (theoretical value = 2447).

EXAMPLE 26 PRODUCTION OF [Leu$^{18}$]-ET-1 (SEQ ID NO:34)

(26-1) The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Leu-Ile-Ile-Trp(For)-O-CH$_2$-Pam resin The resulting peptide resin was further deprotected, oxidized and purified as with Example 1 to obtain the desired product.

Anal. for amino acids: Asp 1.02(1); Ser 2.67(3); Glu 1.07(1); Cyt 1.02(2); Val 0.97(1); Met 0.98(1); Ile 0.79(2); Leu 2.65(3); Tyr 0.91(1); Phe 1.03(1); Lys 1.07(1); His 0.91(1).

LSIMS (M+H+) = 2489 (theoretical value = 2489).

(26-2) The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Leu-Ile-Ile-Trp(For)-O-CH$_2$-Pam resin.

Then, a crude peptide obtained by deprotecting the protected peptide in a manner similar to that of Example 1 was dissolved in 500 ml of a 0.1M aqueous solution of ammonium acetate (pH 8.5) containing 25% ethanol and 25% n-butanol, and oxidized with air with stirring at room temperature for 10 hours. Thereafter, acetic acid was added to the solution to adjust it to pH 5.0, and the solvents were removed by distillation under reduced pressure, followed by lyophilization. The resulting product was purified in a manner similar to that of Example 1 to obtain the desired product.

Anal. for amino acids: Asp 1.00(1); Ser 2.55(3); Glu 1.01(1); Cyt 0.88(2); Val 0.98(1); Met 1.02(1); Ile 1.17(2); Leu 3.11(3); Tyr 0.89(1); Phe 1.02(1); Lys 0.98(1); His 0.99(1).

LSIMS (M+H+) = 2489 (theoretical value = 2489).

EXAMPLE 27 PRODUCTION OF [Val$^{18}$]-ET-1 (SEQ ID NO: 35)

(27-1) The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Val-Ile-Ile-Trp(For)-O-CH$_2$-Pam resin.

The resulting peptide resin was further deprotected, oxidized and purified as with Example 1 to obtain the desired product.

Anal. for amino acids: Asp 1.03(1); Ser 2.66(3); Glu 1.08(1); Cyt 0.95(2); Val 1.68(2); Met 0.99(1); Ile 0.73(2); Leu 1.67(2); Tyr 0.92(1); Phe 1.04(1); Lys 1.05(1); His 0.97(1).

LSIMS (M+H+) = 2475 (theoretical value = 2475).

(27-2) The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Val-Ile-Ile-Trp(for)-O-CH$^2$-Pam resin.

The resulting peptide resin was further deprotected, oxidized and purified as with Example 26-2 to obtain the desired product.

Anal. for amino acids: Asp 1.00(1); Ser 2.43(3); Glu 0.97(1); Cyt 0.76(2); Val 0.99(1); Met 0.95(1); Ile 1.02(2); Leu 2.03(2); Tyr 0.90(1); Phe 0.98(1); Lys 0.99(1); His 0.96(1).

LSIMS (M+H+)=2475 (theoretical value=2475).

EXAMPLE 28 PRODUCTION OF [Gly$^{18}$]-ET-1 (SEQ ID NO: 36)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-Gly-Ile-Ile-Trp(For)-O-CH$_2$-Pam resin.

The resulting peptide resin was further deprotected, oxidized and purified as with Example 1 to obtain the desired product.

Anal. for amino acids: Asp 1.03(1); Ser 2.67(3); Glu 1.06(1); Gly 1.00(1); Cyt 0.,91(2); Val 0.96(1); Met 0.98(1); Ile 1.08(2); Leu 2.07(2); Tyr 0.92(1); Phe 1.02(1); Lys 1.06(1); His 0.97(1).

LSIMS (M+H+)=2433 (theoretical value=2433).

EXAMPLE 29 PRODUCTION OF [D-Ala$^{18}$]-ET-1

The following protected peptide resin was obtained by procedures similar to those of Example 1 except that Boc-D-Ala (Nova) was used:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-D-Ala-Ile-Ile-Trp(For)-O-CH$_2$-Pam resin.

The resulting peptide resin was further deprotected, oxidized and purified as with Example 1 to obtain the desired product.

Anal. for amino acids: Asp 1.02(1); Ser 2.64(3); Glu 1.07(1); Ala 1.00(1); Cyt 0.95(2); Val 0.96(1); Met 0.99(1); Ile 0.96(2); Leu 2.06(2); Tyr 0.93(1); Phe 1.01(1); Lys 1.07(1); His 0.98(1).

LSIMS (M+H+)=2447 (theoretical value=2447).

EXAMPLE 30 PRODUCTION OF [Abu$^{18}$]-ET-1 (SEQ ID NO: 37)

The following protected peptide resin was obtained by procedures similar to those of Example 1 except that Boc-Abu (Nova) was used:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-Abu-Ile-Ile-Trp(For)-O-CH$_2$-Pam resin.

The resulting peptide resin was further deprotected, oxidized and purified as with Example 1 to obtain the desired product.

Anal. for amino acids: Asp 1.03(1); Ser 2.58(3); Glu 1.05(1); Cyt 0.89(2); Val 0.94(1); Met 1.00(1); Ile 0.93(2); Leu 2.03(2); Tyr 0.92(1); Phe 1.00(1); Lys 1.06(1); His 0.97(1).

LSIMS (M+H+)=2461 (theoretical value=2461).

EXAMPLE 31 PRODUCTION OF [Nva$^{18}$]-ET-1 (SEQ ID NO: 38)

(31-1) The following protected peptide resin was obtained by procedures similar to those of Example 1 except that Boc-Nva (Nova) was used:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-Nva-Ile-Ile-Trp(For)-O-CH$_2$-Pam resin.

The resulting peptide resin was further deprotected, oxidized and purified as with Example 1 to obtain the desired product.

Anal. for amino acids: Asp 1.02(1); Ser 2.61(3); Glu 1.06(1); Cyt 0.91(2); Val 0.96(1); Met 1.00(1); Ile 0.81(2); Leu 2.04(2); Tyr 0.92(1); Phe 1.01(1); Lys 1.07(1); His 0.98(1).

LSIMS (M+H+)=2475 (theoretical value=2475).

(31-2) The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-Nva-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.55(3); Glu 1.08(1); Cyt 0.84(2); Val 0.99(1); Met 0.96(1); Ile 1.09(2); Leu 1.99(2); Tyr 0.87(1); Phe 1.02(1); Lys 1.03(1); His 0.98(1).

LSIMS (M+H+)=2475 (theoretical value=2475).

EXAMPLE 32 PRODUCTION OF [Nle$^{18}$]-ET-1 (SEQ ID NO: 39)

(32-1) The following protected peptide resin was obtained by procedures similar to those of Example 1 except that Boc-Nle(Nova)was used:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-Nle-Ile-Ile-Trp(For)-O-CH$_2$-Pam resin.

The resulting peptide resin was further deprotected, oxidized and purified as with Example 1 to obtain the desired product.

Anal. for amino acids: Asp 1.03(1); Ser 2.63(3); Glu 06(1); Cyt 0.93(2); Val 0.97(1); Met 1.00(1); Ile 0.81(2); Leu 1.72(2); Tyr 0.92(1); Phe 1.00(1); Lys 1.08(1); His 0.96(1).

LSIMS (M+H+)=2489 (theoretical value=2489).

(32-2) The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-Nle-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.62(3); Glu 1.04(1); Cyt 0.79(2); Val 0.98(1); Met 1.03(1); Ile 1.13(2); Leu 1.96(2); Tyr 0.82(1); Phe 0.98(1); Lys 0.96(1); His 0.98(1) .

LSIMS (M+H+)=2489 (theoretical value=2489).

EXAMPLE 33 PRODUCTION OF [Phe$^{18}$]-ET-1 (SEQ ID NO: 40)

(33-1) The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(O-cHex)-Cys(MeBzl)-Val-Tyr(BrZ)-Phe-Cys(MeBzl)-His(Dnp)-Leu-Phe-Ile-Ile-Trp(For)-O-CH$_2$-Pam resin.

The resulting peptide resin was further deprotected, oxidized and purified as with Example 1 to obtain the desired product.

Anal. for amino acids: Asp 1.03(1); Ser 2.65(3); Glu 1.05(1); Cyt 0.89(2): Val 0.96(1); Met 1.00(1); Ile 0.79(2);

Leu 1.73(2); Tyr 0.91(1); Phe 1.75(2); Lys 1.06(1); His 0.95(1).

LSIMS (M+H+)=2523 (theoretical value=2523).

(33-2) The following protected peptide resin was obtained by procedures similar to those of Example 1.

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Phe-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.55(3); Glu 0.99(1); Cyt 0.79(2); Val 0.94(1); Met 1.01(1); Ile 1.02(2); Leu 2.02(2); Tyr 0.85(1); Phe 1.99(2); Lys 0.98(1); His 1.00(1).

LSIMS (M+H+)=2523 (theoretical value=2523).

EXAMPLE 34 PRODUCTION OF [Ser$^{18}$]-ET-1 (SEQ ID NO: 41)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Ser(Bzl)-Ile-Ile-Trp(For)-O-CH$_2$-Pam resin.

The resulting peptide resin was further deprotected, oxidized and purified as with Example 1 to obtain the desired product.

Anal. for amino acids: Asp 1.02(1); Ser 3.24(4); Glu 1.06(1); Cyt 0.92(2); Val 0.93(1); Met 1.00(1); Ile 1.02(2); Leu 2.06(2); Tyr 0.91(1); Phe 1.03(1); Lys 1.07(1); His 0.97(1)

LSIMS (M+H+)=2463 (theoretical value=2463).

EXAMPLE 35 PRODUCTION OF [Asn$^{18}$]-ET-1 (SEQ ID NO: 42)

The following protected peptide resin was obtained by procedures similar to those of Example 1 except that Boc-Abu (Nova) was used:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Asn-Ile-Ile-Trp(For)-O-CH$_2$-Pam resin.

The resulting peptide resin was further deprotected, oxidized and purified as with Example 1 to obtain the desired product.

Anal. for amino acids: Asp 2.05(2); Ser 2.56(3); Glu 1.06(1); Cyt 0.93(2); Val 0.95(1); Met 1.00(1); Ile 1.07(2); Leu 2.07(2); Tyr 0.93(1); Phe 1.01(1); Lys 1.05(1); His 0.97(1).

LSIMS (M+H+)=2490 (theoretical value=2490).

EXAMPLE 36 PRODUCTION OF [Ala$^{18}$]-ET-2 (SEQ ID NO: 43)

The following protected peptide resin was obtained by procedures similar to those of Example 1:

Boc-Cys(MeBzl)-Ser(Bzl)-Cys(MeBzl)-Ser(Bzl)-Ser(Bzl)-Trp(For)-Leu-Asp(OcHex)-Lys(ClZ)-Glu(OcHex)-Cys(MeBzl)-Val-Tyr(BrZ)-Phe-Cys(MeBzl)-His(Dnp)-Leu-Ala-Ile-Ile-Trp(For)-O-CH$_2$-Pam resin.

The resulting peptide resin was further deprotected, oxidized and purified as with Example 1 to obtain the desired product.

Anal. for amino acids: Asp 1.03(1); Ser 2.63(3); Glu 1.06(1); Ala 1.00(1); Cyt 0.93(2); Val 0.92(1); Ile 1.03(2); Leu 2.07(2); Tyr 0.91(1); Phe 1.02(1); Lys 1.05(1); His 0.97(1).

LSIMS (M+H+)=2502 (theoretical value=2502).

EXAMPLE 37 PRODUCTION OF [Ala$^{18}$]-ET-3 (SEQ ID NO: 44)

The following protected peptide resin was obtained by procedures similar to those of Example 1:

Boc-Cys(MeBzl)-Thr(Bzl)-Cys(MeBzl)-Phe-Thr(Bzl)-Tyr(BrZ)-Lys(ClZ)-Asp(OcHex)-Lys(ClZ)-Glu(OcHex)-Cys(MeBzl)-Val-Tyr(BrZ)-Tyr(BrZ)-Cys(MeBzl)-His(Dnp)-Leu-Ala-Ile-Ile-Trp(For)-O-CH$_2$-Pam resin.

The resulting peptide resin was further deprotected, oxidized and purified as with Example 1 to obtain the desired product.

Anal. for amino acids: Asp 1.02(1); Thr 1.71(2); Glu 1.06(1); Ala 1.00(1); Cyt 0.97(2); Val 0.93(1); Ile 1.06(2); Leu 1.02(1); Tyr 2.89(3); Phe 1.01(1); Lys 2.04(2); His 0.94(1).

LSIMS (M+H+)=2598 (theoretical value=2598).

EXAMPLE 38 PRODUCTION OF [Leu$^{3,11}$]-ET-1 (SEQ ID NO: 45)

The following protected peptide resin was obtained by procedures similar to those of Example 1:

Boc-Cys(MeBzl)-Ser(Bzl)-Leu-Ser(Bzl)-Ser(Bzl)-Leu-Met-Asp(OcHex)-Lys(ClZ)-Glu(OcHex)-Leu-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.61(3); Glu 0.97(1); Cyt 0.40(1); Val 0.95(1); Met 0.99(1); Ile 1.10(2); Leu 3.96(4); Tyr 0.90(1); Phe 1.00(1); Lys11.04(1); His 0.97(1).

LSIMS (M+H+)=2513 (theoretical value=2513).

EXAMPLE 39 PRODUCTION OF [Val$^{3,11}$]-ET-1 (SEQ ID NO: 46)

The following protected peptide resin was obtained by procedures similar to those of Example 1:

Boc-Cys(MeBzl)-Ser(Bzl)-Val-Ser(Bzl)-Ser(Bzl)-Leu-Met-Asp(OcHex)-Lys(ClZ)-Glu(OcHex)-Val-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.63(3); Glu 1.05(1); Cyt 0.43(1); Val 2.34(3); Met 0.96(1); Ile 1.09(2); Leu 2.00(2); Tyr 0.91(1); Phe 1.01(1); Lys 1.01(1); His 0.98(1).

LSIMS (M+H+)=2485 (theoretical value=2485).

EXAMPLE 40 PRODUCTION OF [Met$^{3,11}$]-ET-1 (SEQ ID NO: 47)

The following protected peptide resin was obtained by procedures similar to those of Example 1:

Boc-Cys(MeBzl)-Ser(Bzl)-Met-Ser(Bzl)-Ser(Bzl)-Leu-Met-Asp(OcHex)-Lys(ClZ)-Glu(OcHex)-Met-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.64(3); Glu 1.05(1); Cyt 0.43(1); Val 0.95(1); Met 2.86(3); Ile 1.11(2);

Leu 1.98(2); Tyr 0.89(1); Phe 1.00(1); Lys 1.02(1); His 0.97(1).

LSIMS (M+H+)=2549 (theoretical value=2549).

EXAMPLE 41 PRODUCTION OF [Val$^{3,11}$]-ET-1 (SEQ ID NO: 48)

The following protected peptide resin was obtained by procedures similar to those of Example 1:

Boc-Cys(MeBzl)-Ser(Bzl)-Val-Ser(Bzl)-Ser(Bzl)-Leu-Met-Asp(OcHex)-Lys(Clz)-Glu(OcHex)-Ala-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.62(3); Glu 1.07(1); Ala 1.01(1); Cyt 0.41(1); Val 1.94(2); Met 0.96(1); Ile 1.10(2); Leu 2.02(2); Tyr 0.89(1); Phe 1.01(1); Lys 1.02(1); His 0.98(1).

LSIMS (M+H+)=2457 (theoretical value=2457).

EXAMPLE 42 PRODUCTION OF [Ser$^{3,11}$]-ET-1 (SEQ ID NO: 49)

The following protected peptide resin was obtained by procedures similar to those of Example 1:

Boc-Cys(MeBzl)-Ser(Bzl)-Ser(Bzl)-Ser(Bzl)-Ser(Bzl)-Leu-Met-Asp(OcHex)-Lys(ClZ)-Glu(OcHex)-Ser(Bzl)-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 3.97(5); Glu 1.07(1); Cyt 0.43(1); Val 0.93(1); Met 0.96(1); Ile 1.08(2); Leu 2.01(2); Tyr 0.90(1); Phe 1.01(1); Lys 1.01(1); His 0.97(1).

LSIMS (M+H+)=2460 (theoretical value=2460).

EXAMPLE 43 PRODUCTION OF [Ile$^{18}$]-ET-1 (SEQ ID NO: 50)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Ile-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.61(3); Glu 0.98(1); Cyt 0.82(2); Val 1.00(1); Met 0.96(1); Ile 1.52(3); Leu 1.97(2); Tyr 0.90(1) Phe 1.08(1); Lys 1.01(1); His 0.98(1).

LSIMS (M+H+)=2489 (theoretical value=2489).

EXAMPLE 44 PRODUCTION OF [t-Leu$^{18}$]-ET-1 (SEQ ID NO: 51)

The following protected peptide resin was obtained by procedures similar to those of Example 1 except that Boc-t-Leu (Daiichi Kagaku Yakuhin) was used:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-t-Leu-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.61(3); Glu 0.98(1); Cyt 0 88(2); Val 0.96(1); Met 1.00(1); Ile 1.11(2); Leu 2.04(2); Tyr 0.90(1); Phe 1.06(1); Lys 1.08(1); His 0.99(1).

LSIMS (M+H+)=2489 (theoretical value=2489).

EXAMPLE 45 PRODUCTION OF [γ-Leu$^{18}$]-ET-1 (SEQ ID NO: 52)

The following protected peptide resin was obtained by procedures similar to those of Example 1 except that Boc-γ-Leu prepared by protecting γ-Leu (Daiichi Kagaku Yakuhin) with a Boc group using (Boc)$_2$O was used:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-γ-Leu-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.53(3); Glu 1.02(1); Cyt 0.85(2); Val 1.04(1); Met 0.96(1); Ile 1.02(2); Leu 2.08(2); Tyr 0.82(1); Phe 0.98(1); Lys 1.00(1); His 1.03(1).

LSIMS (M+H+)=2503 (theoretical value=2503).

EXAMPLE 46 PRODUCTION OF [Glu$^{18}$]-ET-1 (SEQ ID NO: 53)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Glu(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 1.00(1); Ser 2.56(3); Glu 2.08(2); Cyt 0.89(2); Val 0.98(1); Met 0.95(1); Ile 1.09(2); Leu 1.96(2); Tyr 0.84(1); Phe 1.05(1); Lys 0.97(1); His 1.01(1).

LSIMS (M+H+)=2505 (theoretical value=2505).

EXAMPLE 47 PRODUCTION OF [Lys$^{18}$]-ET-1 (SEQ ID NO: 54)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Lys(ClZ)-Ile-Ile-Trp(For)-O-CH$_2$-Pam resin.

The resulting peptide resin was further deprotected, oxidized and purified as with Example 1 to obtain the desired product.

Anal. for amino acids: Asp 1.00(1); Ser 2.63(3); Glu 0.96(1); Cyt 0.91(2); Val 0.99(1); Met 0.97(1); Ile 1.12(2); Leu 1.97(2); Tyr 0.84(1); Phe 1.01(1); Lys 2.18(2); His 1.01(1).

LSIMS (M+H+)=2504 (theoretical value=2504).

EXAMPLE 48 PRODUCTION OF [Leu$^{9,18}$]-ET-1 (SEQ ID NO: 55)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Leu-Glu(OcHex)-Cys(MeBzl)-Val-Tyr(BrZ)-Phe-Cyhs(MeBzl)-His(Dnp)-Leu-Leu-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.59(3); Glu 0.99(1); Cyt 0.88(2); Val 1.02(1); Met 0.97(1); Ile 1.13(2); Leu 4.19(4); Tyr 0.90(1); Phe 0.96(1); His 0.98(1).

LSIMS (M+H+)=2474 (theoretical value=2474).

EXAMPLE 49 PRODUCTION OF [Ile$^{18}$]-ET-2 (SEQ ID NO: 56)

The following protected peptide resin was obtained by procedures similar to those of Example 1:

Boc-Cys(MeBzl)-Ser(Bzl)-Cys(MeBzl)-Ser(Bzl)-Ser(Bzl)-Trp(For)-Leu-Asp(OcHex)-Lys(ClZ)-Glu(OcHex)-Cys(MeBzl)-Val-Tyr(BrZ)-Phe-Cys(MeBzl)-His(Dnp)-Leu-Ile-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.64(3); Glu 1.08(1); Cyt 0.85(2); Val 1.00(1); Ile 1.52(3); Leu 1.95(2); Tyr 0.86(1); Phe 1.10(1); Lys 0.95(1); His 1.02(1).

LSIMS (M+H+)=2544 (theoretical value=2544).

EXAMPLE 50 PRODUCTION OF [Ile$^{18}$]-ET-3 (SEQ ID NO: 57)

The following protected peptide resin was obtained by procedures similar to those of Example 1:

Boc-Cys(MeBzl)-Thr(Bzl)-Cys(MeBzl)-Phe-Thr(Bzl)-Tyr(BrZ)-Lys(ClZ)-Asp(OcHex)-Lys(ClZ)-Glu(OcHex) Cys(MeBzl)-Val-Tyr(BrZ)-Tyr(BrZ)-Cys(MeBzl)-His(Dnp)-Leu-Ile-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Thr 1.78(2); Glu 0.99(1); Cyt 0.88(2); Val 1.02(1); Ile 1.54(3); Leu 1.03(1); Tyr 2.66(3); Phe 1.02(1); Lys 2.04(2); His 1.01(1).

LSIMS (M+H+)=2640 (theoretical value=2640).

EXAMPLE 51 PRODUCTION OF [Thr$^{18}$]-ET-1 (SEQ ID NO: 58)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Thr(Bzl)-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.00(1); Ser 2.51(3); Thr 0.82(1); Glu 0.96(1); Cyt 0.88(2); Val 1.02(1); Met 0.98(1); Ile 1.06(2); Leu 2.16(2); Tyr 0.87(1); Phe 0.99(1); Lys 1.03(1); His 0.98(1).

LSIMS (M+H+)=2477 (theoretical value=2477).

EXAMPLE 52 PRODUCTION OF [Leu$^3$, Ala$^{11}$]-ET-1 (SEQ ID NO: 59)

The following protected peptide resin was obtained by procedures similar to those of Example 1:

Boc-Cys(MeBzl)-Ser(Bzl)-Leu-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 2.00(2); Ser 2.48(3); Glu 1.01(1); Ala 1.09(1); Cyt 0.46(1); Val 0.96(1); Met 0.93(1); Ile 1.06(2); Leu 2.95(3); Tyr 0.91(1); Phe 0.98(1); Lys 1.02(1); His 0.97(1).

LSIMS (M+H+)=2471 (theoretical value=2471).

Example 53 PRODUCTION OF [Nal(2)$^{3,11}$]-ET-1 (SEQ ID NO: 60)

The following protected peptide resin was obtained by procedures similar to those of Example 1, using Boc-Nal(2) obtained by reacting Nal(2)(BACHEM) with (Boc)$_2$O:

Boc-Cys(MeBzl)-Ser(Bzl)-Nal(2)-Ser(Bzl)-Ser(Bzl)-Leu-Met-Asp(OcHex)-Lys(ClZ)-Glu(OcHex)-Nal(2)-Val-Tyr(BrZ)-Phe-Cys(MeBzl)-His(Dnp)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 1.98(2); Ser 2.64(3); Glu 1.09(1); Cyt 0.40(1); Val 0.91(1); Met 0.97(1); Ile 0.92(2); Leu 2.01(2); Tyr 0.85(1); Phe 0.95(1); Lys 1.01(1); His 0.99(1).

LSIMS (M+H+)=2681 (theoretical value=2681).

EXAMPLE 54 PRODUCTION OF [Met$^{18}$]-ET-1 (SEQ ID NO: 61)

The following protected peptide resin was obtained by procedures similar to those of Example 1:

Boc-Cys(MeBzl)-Ser(Bzl)-Cys(MeBzl)-Ser(Bzl)-Ser(Bzl)-Leu-Met-Asp(OcHex)-Lys(ClZ)-Glu(OcHex)-Cys(MeBzl)-Val-Tyr(BrZ)-Phe-Cys(MeBzl)-His(Dnp)-Leu-Met-Ile-Ile-Trp(For)-O-CH$_2$-Pam resin.

The resulting peptide resin was further deprotected, oxidized and purified as with Example 26-2 to obtain the desired product.

Anal. for amino acids: Asp 1.03(1); Ser 2.58(3); Glu 1.10(1); Cyt 0.93(2); Val 0.93(1); Met 1.89(1); Ile 0.83(2); Leu 1.90(2); Tyr 0.92(1) Phe 1.01(1); Lys 1.00(1); His 0.98(1).

LSIMS (M+H+)=2507 (theoretical value=2507).

REFERENCE EXAMPLE 1 PRODUCTION OF [Ala$^{3,11}$, des His$^{16}$]-ET-1 (SEQ ID NO: 62)

The following protected peptide resin was obtained by procedures similar to those of Example 1:

Boc-Cys(MeBzl)-Ser(Bzl)-Ala-Ser(Bzl)-Ser(Bzl)-Leu-Met-Asp(OcHex)-Lys(ClZ)-Glu(OcHex)-Ala-Val-Tyr(BrZ)-Phe-Cys(MeBzl)-Leu-Asp(OcHex)-Ile-Ile-Trp(For)-O-CH$_2$-Pam resin.

The resulting peptide resin was further deprotected, oxidized and purified as with Example 1 to obtain the desired product.

Anal. for amino acids: Asp 1.96(2); Ser 2.84(3); Glu 1.13(1); Ala 2.00(2); Cyt 0.41(2); Val 0.62(1); Met 1.04(1); Ile 0.60(2); Leu 1.84(2); Tyr 0.54(1); Phe 0.79(1); Lys 1.14(1).

LSIMS (M+H+)=2292 (theoretical value=2292).

What is claimed is:

1. The peptide having an amino acid sequence selected from the group consisting of SEQ ID NO: 9, SEQ ID NO: 10, SEQ ID NO: 11, SEQ ID NO: 12, SEQ ID NO: 21, SEQ ID NO: 29, SEQ ID NO: 30, SEQ ID NO: 31, SEQ ID NO: 34, SEQ ID NO: 35, SEQ ID NO: 37, SEQ ID NO: 38, SEQ ID NO: 40, SEQ ID NO: 45, SEQ ID NO: 50, SEQ ID NO: 52, SEQ ID NO: 53, and SEQ ID NO: 59 or a pharmaceutically acceptable salt thereof.

* * * * *

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( x i ) SEQUENCE DESCRIPTION: SEQ ID NO:1:

Cys Ser Cys Ser Ser Leu Met Asp Lys Glu Cys Val Tyr Phe Cys His
1               5                   10                  15

Leu Asp Ile Ile Trp
            20

( 2 ) INFORMATION FOR SEQ ID NO:2:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( x i ) SEQUENCE DESCRIPTION: SEQ ID NO:2:

Cys Ser Cys Ser Ser Trp Leu Asp Lys Glu Cys Val Tyr Phe Cys His
1               5                   10                  15

Leu Asp Ile Ile Trp
            20

( 2 ) INFORMATION FOR SEQ ID NO:3:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( x i ) SEQUENCE DESCRIPTION: SEQ ID NO:3:

Cys Thr Cys Phe Thr Tyr Lys Asp Lys Glu Cys Val Tyr Tyr Cys His
1               5                   10                  15

Leu Asp Ile Ile Trp
            20

( 2 ) INFORMATION FOR SEQ ID NO:4:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( i x ) FEATURE:
( A ) NAME/KEY: modified-site
( B ) LOCATION: 3 and/or 11
( D ) OTHER INFORMATION: amino acid other than L-Ala or other than L- Cys;

( i x ) FEATURE:
( A ) NAME/KEY: modified-site ( B ) LOCATION: 9
                ( D ) OTHER INFORMATION: amino acid other than L-Lys;
                        or ( i x ) FEATURE:
                ( A ) NAME/KEY: modified-site
                ( B ) LOCATION: 18
                ( D ) OTHER INFORMATION: amino acid other than L-Asp ( x i ) SEQUENCE DESCRIPTION: SEQ ID NO:4:

Cys  Ser  Xaa  Ser  Ser  Leu  Met  Asp  Xaa  Glu  Xaa  Val  Tyr  Phe  Cys  His
    1                   5                        10                       15

Leu  Xaa  Ile  Ile  Trp
                    20

( 2 ) INFORMATION FOR SEQ ID NO:5:

( i ) SEQUENCE CHARACTERISTICS:
                ( A ) LENGTH: 21 amino acids
                ( B ) TYPE: amino acid
                ( D ) TOPOLOGY: linear ( i i ) MOLECULE TYPE: protein ( i x ) FEATURE:
                ( A ) NAME/KEY: modified-site
                ( B ) LOCATION: 3 and/or 11
                ( D ) OTHER INFORMATION: amino acid other than L-Ala or other
                        than L- Cys;

( i x ) FEATURE:
                ( A ) NAME/KEY: modified-site
                ( B ) LOCATION: 9
                ( D ) OTHER INFORMATION: amino acid other than L-Lys;
                        or ( i x ) FEATURE:
                ( A ) NAME/KEY: modified-site
                ( B ) LOCATION: 18
                ( D ) OTHER INFORMATION: amino acid other than L-Asp ( x i ) SEQUENCE DESCRIPTION: SEQ ID NO:5:

Cys  Ser  Xaa  Ser  Ser  Trp  Leu  Asp  Xaa  Glu  Xaa  Val  Tyr  Phe  Cys  His
    1                   5                        10                       15

Leu  Xaa  Ile  Ile  Trp
                    20

( 2 ) INFORMATION FOR SEQ ID NO:6:

( i ) SEQUENCE CHARACTERISTICS:
                ( A ) LENGTH: 21 amino acids
                ( B ) TYPE: amino acid
                ( D ) TOPOLOGY: linear ( i i ) MOLECULE TYPE: protein ( i x ) FEATURE:
                ( A ) NAME/KEY: modified-site
                ( B ) LOCATION: 3 and/or 11
                ( D ) OTHER INFORMATION: amino acid other than L-Ala or other
                        than L- Cys;

( i x ) FEATURE:
                ( A ) NAME/KEY: modified-site
                ( B ) LOCATION: 9
                ( D ) OTHER INFORMATION: amino acid other than L-Lys;
                        or ( i x ) FEATURE:
                ( A ) NAME/KEY: modified-site
                ( B ) LOCATION: 18
                ( D ) OTHER INFORMATION: amino acid other than L-Asp ( x i ) SEQUENCE DESCRIPTION: SEQ ID NO:6:

Cys  Thr  Xaa  Phe  Thr  Tyr  Lys  Asp  Xaa  Glu  Xaa  Val  Tyr  Tyr  Cys  His

```
          1               5                    10                   15
    Leu  Xaa  Ile  Ile  Trp
                    20
```

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:7:

```
    Cys  Ser  Cys  Asn  Ser  Trp  Leu  Asp  Lys  Glu  Cys  Val  Tyr  Phe  Cys  His
     1                5                    10                              15
    Leu  Asp  Ile  Ile  Trp
                    20
```

(2) INFORMATION FOR SEQ ID NO:8:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:8:

```
    Cys  Ser  Ala  Ser  Ser  Leu  Met  Asp  Lys  Glu  Ala  Val  Tyr  Phe  Cys  His
     1                5                    10                              15
    Leu  Asp  Ile  Ile  Trp
                    20
```

(2) INFORMATION FOR SEQ ID NO:9:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:9:

```
    Cys  Ser  Phe  Ser  Ser  Leu  Met  Asp  Lys  Glu  Phe  Val  Tyr  Phe  Cys  His
     1                5                    10                              15
    Leu  Asp  Ile  Ile  Trp
                    20
```

(2) INFORMATION FOR SEQ ID NO:10:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:10:

```
    Cys  Ser  Phe  Ser  Ser  Leu  Met  Asp  Lys  Glu  Ala  Val  Tyr  Phe  Cys  His
     1                5                    10                              15
    Leu  Asp  Ile  Ile  Trp
                    20
```

(2) INFORMATION FOR SEQ ID NO:11:

(i) SEQUENCE CHARACTERISTICS:
        (A) LENGTH: 21 amino acids (B) TYPE: amino acid
(D) TOPOLOGY: linear (i i) MOLECULE TYPE: protein (x i) SEQUENCE DESCRIPTION: SEQ ID NO:11:

Cys Ser Ala Ser Ser Leu Met Asp Lys Glu Phe Val Tyr Phe Cys His
1               5                   10                  15

Leu Asp Ile Ile Trp
            20

(2) INFORMATION FOR SEQ ID NO:12:

(i) SEQUENCE CHARACTERISTICS:
    (A) LENGTH: 21 amino acids
    (B) TYPE: amino acid
    (D) TOPOLOGY: linear (i i) MOLECULE TYPE: protein (x i) SEQUENCE DESCRIPTION: SEQ ID NO:12:

Cys Ser Trp Ser Ser Leu Met Asp Lys Glu Trp Val Tyr Phe Cys His
1               5                   10                  15

Leu Asp Ile Ile Trp
            20

(2) INFORMATION FOR SEQ ID NO:13:

(i) SEQUENCE CHARACTERISTICS:
    (A) LENGTH: 21 amino acids
    (B) TYPE: amino acid
    (D) TOPOLOGY: linear (i i) MOLECULE TYPE: protein (i x) FEATURE:
    (A) NAME/KEY: modified-site
    (B) LOCATION: 3
    (D) OTHER INFORMATION: cyclohexylalanine (i x) FEATURE:
    (A) NAME/KEY: modified-site
    (B) LOCATION: 11
    (D) OTHER INFORMATION: cyclohexylalanine (x i) SEQUENCE DESCRIPTION: SEQ ID NO:13:

Cys Ser Xaa Ser Ser Leu Met Asp Lys Glu Xaa Val Tyr Phe Cys His
1               5                   10                  15

Leu Asp Ile Ile Trp
            20

(2) INFORMATION FOR SEQ ID NO:14:

(i) SEQUENCE CHARACTERISTICS:
    (A) LENGTH: 21 amino acids
    (B) TYPE: amino acid
    (D) TOPOLOGY: linear (i i) MOLECULE TYPE: protein (i x) FEATURE:
    (A) NAME/KEY: modified-site
    (B) LOCATION: 3
    (D) OTHER INFORMATION: 1- naphthylalanine (i x) FEATURE:
    (A) NAME/KEY: modified-site
    (B) LOCATION: 11
    (D) OTHER INFORMATION: 1- naphthylalanine (x i) SEQUENCE DESCRIPTION: SEQ ID NO:14:

Cys Ser Xaa Ser Ser Leu Met Asp Lys Glu Xaa Val Tyr Phe Cys His

```
            1               5                    10                   15
```

Leu Asp Ile Ile Trp
              20

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Cys Ser His Ser Ser Leu Met Asp Lys Glu His Val Tyr Phe Cys His
1               5                    10                   15
```

Leu Asp Ile Ile Trp
              20

( 2 ) INFORMATION FOR SEQ ID NO:16:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Cys Ser Tyr Ser Ser Leu Met Asp Lys Glu Tyr Val Tyr Phe Cys His
1               5                    10                   15
```

Leu Asp Ile Ile Trp
              20

( 2 ) INFORMATION FOR SEQ ID NO:17:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: Beta-2- Thienylalanine ( i x ) FEATURE:
        ( A ) NAME/KEY: modified-site
        ( B ) LOCATION: 11
        ( D ) OTHER INFORMATION: Beta-2- Thienylalanine ( x i ) SEQUENCE DESCRIPTION: SEQ ID NO:17:

```
Cys Ser Xaa Ser Ser Leu Met Asp Lys Glu Xaa Val Tyr Phe Cys His
1               5                    10                   15
```

Leu Asp Ile Ile Trp
              20

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3

( D ) OTHER INFORMATION: 4- Fluorophenylalanine ( i x ) FEATURE:
    ( A ) NAME/KEY: modified-site
    ( B ) LOCATION: 11
    ( D ) OTHER INFORMATION: 4- Fluorophenylalanine ( x i ) SEQUENCE DESCRIPTION: SEQ ID NO:18:

```
Cys Ser Xaa Ser Ser Leu Met Asp Lys Glu Xaa Val Tyr Phe Cys His
1               5                   10                      15

Leu Asp Ile Ile Trp
            20
```

( 2 ) INFORMATION FOR SEQ ID NO:19:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: Phenylglycine ( i x ) FEATURE:
        ( A ) NAME/KEY: modified-site
        ( B ) LOCATION: 11
        ( D ) OTHER INFORMATION: Phenylglycine ( x i ) SEQUENCE DESCRIPTION: SEQ ID NO:19:

```
Cys Ser Xaa Ser Ser Leu Met Asp Lys Glu Xaa Val Tyr Phe Cys His
1               5                   10                      15

Leu Asp Ile Ile Trp
            20
```

( 2 ) INFORMATION FOR SEQ ID NO:20:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: O- Ethyltyrosine ( i x ) FEATURE:
        ( A ) NAME/KEY: modified-site
        ( B ) LOCATION: 11
        ( D ) OTHER INFORMATION: O- Ethyltyrosine ( x i ) SEQUENCE DESCRIPTION: SEQ ID NO:20:

```
Cys Ser Xaa Ser Ser Leu Met Asp Lys Glu Xaa Val Tyr Phe Cys His
1               5                   10                      15

Leu Asp Ile Ile Trp
            20
```

( 2 ) INFORMATION FOR SEQ ID NO:21:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
      Cys  Ser  Trp  Ser  Ser  Leu  Met  Asp  Lys  Glu  Ala  Val  Tyr  Phe  Cys  His
      1              5                        10                            15

Leu  Asp  Ile  Ile  Trp
                    20
```

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: 1- Naphthylalanine ( x i ) SEQUENCE DESCRIPTION: SEQ ID NO:22:

```
      Cys  Ser  Xaa  Ser  Ser  Leu  Met  Asp  Lys  Glu  Ala  Val  Tyr  Phe  Cys  His
      1              5                        10                            15

Leu  Asp  Ile  Ile  Trp
                    20
```

( 2 ) INFORMATION FOR SEQ ID NO:23:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: 2- Naphthylalanine ( x i ) SEQUENCE DESCRIPTION: SEQ ID NO:23:

```
      Cys  Ser  Xaa  Ser  Ser  Leu  Met  Asp  Lys  Glu  Ala  Val  Tyr  Phe  Cys  His
      1              5                        10                            15

Leu  Asp  Ile  Ile  Trp
                    20
```

( 2 ) INFORMATION FOR SEQ ID NO:24:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: Phenylglycine ( x i ) SEQUENCE DESCRIPTION: SEQ ID NO:24:

```
      Cys  Ser  Xaa  Ser  Ser  Leu  Met  Asp  Lys  Glu  Ala  Val  Tyr  Phe  Cys  His
      1              5                        10                            15

Leu  Asp  Ile  Ile  Trp
                    20
```

( 2 ) INFORMATION FOR SEQ ID NO:25:

( i ) SEQUENCE CHARACTERISTICS:
        ( A ) LENGTH: 21 amino acids
        ( B ) TYPE: amino acid ( D ) TOPOLOGY: linear ( i i ) MOLECULE TYPE: protein ( i x ) FEATURE:
    ( A ) NAME/KEY: modified-site
    ( B ) LOCATION: 3
    ( D ) OTHER INFORMATION: Cyclohexylalanine ( x i ) SEQUENCE DESCRIPTION: SEQ ID NO:25:

```
Cys  Ser  Xaa  Ser  Ser  Leu  Met  Asp  Lys  Glu  Ala  Val  Tyr  Phe  Cys  His
1                  5                        10                            15

Leu  Asp  Ile  Ile  Trp
              20
```

( 2 ) INFORMATION FOR SEQ ID NO:26:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: Beta-2- Thienylalanine ( x i ) SEQUENCE DESCRIPTION: SEQ ID NO:26:

```
Cys  Ser  Xaa  Ser  Ser  Leu  Met  Asp  Lys  Glu  Ala  Val  Tyr  Phe  Cys  His
1                  5                        10                            15

Leu  Asp  Ile  Ile  Trp
              20
```

( 2 ) INFORMATION FOR SEQ ID NO:27:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: O- Ethyltyrosine ( x i ) SEQUENCE DESCRIPTION: SEQ ID NO:27:

```
Cys  Ser  Xaa  Ser  Ser  Leu  Met  Asp  Lys  Glu  Ala  Val  Tyr  Phe  Cys  His
1                  5                        10                            15

Leu  Asp  Ile  Ile  Trp
              20
```

( 2 ) INFORMATION FOR SEQ ID NO:28:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 3
        ( D ) OTHER INFORMATION: 4- Fluorophenylalanine ( x i ) SEQUENCE DESCRIPTION: SEQ ID NO:28:

```
Cys  Ser  Xaa  Ser  Ser  Leu  Met  Asp  Lys  Glu  Ala  Val  Tyr  Phe  Cys  His
1                  5                        10                            15
```

Leu Asp Ile Ile Trp
         20

(2) INFORMATION FOR SEQ ID NO:29:

(i) SEQUENCE CHARACTERISTICS:
      (A) LENGTH: 21 amino acids
      (B) TYPE: amino acid
      (D) TOPOLOGY: linear (ii) MOLECULE TYPE: protein (xi) SEQUENCE DESCRIPTION: SEQ ID NO:29:

Cys Ser Ala Ser Ser Leu Met Asp Lys Glu Ala Val Tyr Phe Cys His
1               5                   10                  15

Leu Ala Ile Ile Trp
         20

(2) INFORMATION FOR SEQ ID NO:30:

(i) SEQUENCE CHARACTERISTICS:
      (A) LENGTH: 21 amino acids
      (B) TYPE: amino acid
      (D) TOPOLOGY: linear (ii) MOLECULE TYPE: protein (xi) SEQUENCE DESCRIPTION: SEQ ID NO:30:

Cys Ser Ala Ser Ser Leu Met Asp Lys Glu Ala Val Tyr Phe Cys His
1               5                   10                  15

Leu Leu Ile Ile Trp
         20

(2) INFORMATION FOR SEQ ID NO:31:

(i) SEQUENCE CHARACTERISTICS:
      (A) LENGTH: 21 amino acids
      (B) TYPE: amino acid
      (D) TOPOLOGY: linear (ii) MOLECULE TYPE: protein (xi) SEQUENCE DESCRIPTION: SEQ ID NO:31:

Cys Ser Ala Ser Ser Leu Met Asp Lys Glu Ala Val Tyr Phe Cys His
1               5                   10                  15

Leu Phe Ile Ile Trp
         20

(2) INFORMATION FOR SEQ ID NO:32:

(i) SEQUENCE CHARACTERISTICS:
      (A) LENGTH: 21 amino acids
      (B) TYPE: amino acid
      (D) TOPOLOGY: linear (ii) MOLECULE TYPE: protein (xi) SEQUENCE DESCRIPTION: SEQ ID NO:32:

Cys Ser Ala Ser Ser Leu Met Asp Lys Glu Ala Val Tyr Phe Cys His
1               5                   10                  15

Leu Gly Ile Ile Trp
         20

(2) INFORMATION FOR SEQ ID NO:33:

(i) SEQUENCE CHARACTERISTICS:
      (A) LENGTH: 21 amino acids
      (B) TYPE: amino acid (D) TOPOLOGY: linear (ii) MOLECULE TYPE: protein (xi) SEQUENCE DESCRIPTION: SEQ ID NO:33:

Cys Ser Cys Ser Ser Leu Met Asp Lys Glu Cys Val Tyr Phe Cys His
1               5                   10                  15

Leu Ala Ile Ile Trp
            20

(2) INFORMATION FOR SEQ ID NO:34:

(i) SEQUENCE CHARACTERISTICS:
    (A) LENGTH: 21 amino acids
    (B) TYPE: amino acid
    (D) TOPOLOGY: linear (ii) MOLECULE TYPE: protein (xi) SEQUENCE DESCRIPTION: SEQ ID NO:34:

Cys Ser Cys Ser Ser Leu Met Asp Lys Glu Cys Val Tyr Phe Cys His
1               5                   10                  15

Leu Leu Ile Ile Trp
            20

(2) INFORMATION FOR SEQ ID NO:35:

(i) SEQUENCE CHARACTERISTICS:
    (A) LENGTH: 21 amino acids
    (B) TYPE: amino acid
    (D) TOPOLOGY: linear (ii) MOLECULE TYPE: protein (xi) SEQUENCE DESCRIPTION: SEQ ID NO:35:

Cys Ser Cys Ser Ser Leu Met Asp Lys Glu Cys Val Tyr Phe Cys His
1               5                   10                  15

Leu Val Ile Ile Trp
            20

(2) INFORMATION FOR SEQ ID NO:36:

(i) SEQUENCE CHARACTERISTICS:
    (A) LENGTH: 21 amino acids
    (B) TYPE: amino acid
    (D) TOPOLOGY: linear (ii) MOLECULE TYPE: protein (xi) SEQUENCE DESCRIPTION: SEQ ID NO:36:

Cys Ser Cys Ser Ser Leu Met Asp Lys Glu Cys Val Tyr Phe Cys His
1               5                   10                  15

Leu Gly Ile Ile Trp
            20

(2) INFORMATION FOR SEQ ID NO:37:

(i) SEQUENCE CHARACTERISTICS:
    (A) LENGTH: 21 amino acids
    (B) TYPE: amino acid
    (D) TOPOLOGY: linear (ii) MOLECULE TYPE: protein (ix) FEATURE:
    (A) NAME/KEY: modified-site
    (B) LOCATION: 18
    (D) OTHER INFORMATION: Abu (xi) SEQUENCE DESCRIPTION: SEQ ID NO:37:

```
Cys  Ser  Cys  Ser  Ser  Leu  Met  Asp  Lys  Glu  Cys  Val  Tyr  Phe  Cys  His
1                   5                        10                            15

Leu  Xaa  Ile  Ile  Trp
              20
```

( 2 ) INFORMATION FOR SEQ ID NO:38:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: protein ( i x ) FEATURE:
      ( A ) NAME/KEY: modified-site
      ( B ) LOCATION: 18
      ( D ) OTHER INFORMATION: Nva ( x i ) SEQUENCE DESCRIPTION: SEQ ID NO:38:

```
Cys  Ser  Cys  Ser  Ser  Leu  Met  Asp  Lys  Glu  Cys  Val  Tyr  Phe  Cys  His
1                   5                        10                            15

Leu  Val  Ile  Ile  Trp
              20
```

( 2 ) INFORMATION FOR SEQ ID NO:39:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: protein ( i x ) FEATURE:
      ( A ) NAME/KEY: modified-site
      ( B ) LOCATION: 18
      ( D ) OTHER INFORMATION: Nle ( x i ) SEQUENCE DESCRIPTION: SEQ ID NO:39:

```
Cys  Ser  Cys  Ser  Ser  Leu  Met  Asp  Lys  Glu  Cys  Val  Tyr  Phe  Cys  His
1                   5                        10                            15

Leu  Leu  Ile  Ile  Trp
              20
```

( 2 ) INFORMATION FOR SEQ ID NO:40:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: protein ( x i ) SEQUENCE DESCRIPTION: SEQ ID NO:40:

```
Cys  Ser  Cys  Ser  Ser  Leu  Met  Asp  Lys  Glu  Cys  Val  Tyr  Phe  Cys  His
1                   5                        10                            15

Leu  Phe  Ile  Ile  Trp
              20
```

( 2 ) INFORMATION FOR SEQ ID NO:41:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: protein ( x i ) SEQUENCE DESCRIPTION: SEQ ID NO:41:

```
Cys  Ser  Cys  Ser  Ser  Leu  Met  Asp  Lys  Glu  Cys  Val  Tyr  Phe  Cys  His
 1              5                        10                            15

Leu  Ser  Ile  Ile  Trp
                20
```

(2) INFORMATION FOR SEQ ID NO:42:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:42:

```
Cys  Ser  Cys  Ser  Ser  Leu  Met  Asp  Lys  Glu  Cys  Val  Tyr  Phe  Cys  His
 1              5                        10                            15

Leu  Asn  Ile  Ile  Trp
                20
```

(2) INFORMATION FOR SEQ ID NO:43:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:43:

```
Cys  Ser  Cys  Ser  Ser  Trp  Leu  Asp  Lys  Glu  Cys  Val  Tyr  Phe  Cys  His
 1              5                        10                            15

Leu  Ala  Ile  Ile  Trp
                20
```

(2) INFORMATION FOR SEQ ID NO:44:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:44:

```
Cys  Thr  Cys  Phe  Thr  Tyr  Lys  Asp  Lys  Glu  Cys  Val  Tyr  Tyr  Cys  His
 1              5                        10                            15

Leu  Ala  Ile  Ile  Trp
                20
```

(2) INFORMATION FOR SEQ ID NO:45:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:45:

```
Cys  Ser  Leu  Ser  Ser  Leu  Met  Asp  Lys  Glu  Leu  Val  Tyr  Phe  Cys  His
 1              5                        10                            15

Leu  Asp  Ile  Ile  Trp
                20
```

(2) INFORMATION FOR SEQ ID NO:46:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: protein ( x i ) SEQUENCE DESCRIPTION: SEQ ID NO:46:

Cys Ser Val Ser Ser Leu Met Asp Lys Glu Val Val Tyr Phe Cys His
1               5                   10                  15

Leu Asp Ile Ile Trp
            20

( 2 ) INFORMATION FOR SEQ ID NO:47:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:47:

Cys Ser Met Ser Ser Leu Met Asp Lys Glu Met Val Tyr Phe Cys His
1               5                   10                  15

Leu Asp Ile Ile Trp
            20

( 2 ) INFORMATION FOR SEQ ID NO:48:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

Cys Ser Val Ser Ser Leu Met Asp Lys Glu Ala Val Tyr Phe Cys His
1               5                   10                  15

Leu Asp Ile Ile Trp
            20

( 2 ) INFORMATION FOR SEQ ID NO:49:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

Cys Ser Ser Ser Ser Leu Met Asp Lys Glu Ser Val Tyr Phe Cys His
1               5                   10                  15

Leu Asp Ile Ile Trp
            20

( 2 ) INFORMATION FOR SEQ ID NO:50:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

Cys Ser Cys Ser Ser Leu Met Asp Lys Glu Cys Val Tyr Phe Cys His

```
                1               5                        1 0                      1 5

Leu  Ile  Ile  Ile  Trp
                      2 0
```

( 2 ) INFORMATION FOR SEQ ID NO:51:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 18
        ( D ) OTHER INFORMATION: tertiary- Leu ( x i ) SEQUENCE DESCRIPTION: SEQ ID NO:51:

```
        Cys  Ser  Cys  Ser  Ser  Leu  Met  Asp  Lys  Glu  Cys  Val  Tyr  Phe  Cys  His
        1                   5                        1 0                      1 5

Leu  Xaa  Ile  Ile  Trp
                      2 0
```

( 2 ) INFORMATION FOR SEQ ID NO:52:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i x ) FEATURE:
        ( A ) NAME/KEY: modified-site
        ( B ) LOCATION: 18
        ( D ) OTHER INFORMATION: gamma- Leu ( x i ) SEQUENCE DESCRIPTION: SEQ ID NO:52:

```
        Cys  Ser  Cys  Ser  Ser  Leu  Met  Asp  Lys  Glu  Cys  Val  Tyr  Phe  Cys  His
        1                   5                        1 0                      1 5

Leu  Xaa  Ile  Ile  Trp
                      2 0
```

( 2 ) INFORMATION FOR SEQ ID NO:53:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
        Cys  Ser  Cys  Ser  Ser  Leu  Met  Asp  Lys  Glu  Cys  Val  Tyr  Phe  Cys  His
        1                   5                        1 0                      1 5

Leu  Glu  Ile  Ile  Trp
                      2 0
```

( 2 ) INFORMATION FOR SEQ ID NO:54:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:54:

```
        Cys  Ser  Cys  Ser  Ser  Leu  Met  Asp  Lys  Glu  Cys  Val  Tyr  Phe  Cys  His
```

Leu Lys Ile Ile Trp
20

( 2 ) INFORMATION FOR SEQ ID NO:55:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:55:

Cys Ser Cys Ser Ser Leu Met Asp Leu Glu Cys Val Tyr Phe Cys His
1               5                   10                  15
Leu Leu Ile Ile Trp
20

( 2 ) INFORMATION FOR SEQ ID NO:56:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

Cys Ser Cys Ser Ser Trp Leu Asp Lys Glu Cys Val Tyr Phe Cys His
1               5                   10                  15
Leu Ile Ile Ile Trp
20

( 2 ) INFORMATION FOR SEQ ID NO:57:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

Cys Thr Cys Phe Thr Tyr Lys Asp Lys Glu Cys Val Tyr Tyr Cys His
1               5                   10                  15
Leu Ile Ile Ile Trp
20

( 2 ) INFORMATION FOR SEQ ID NO:58:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

Cys Ser Cys Ser Ser Leu Met Asp Lys Glu Cys Val Tyr Phe Cys His
1               5                   10                  15
Leu Thr Ile Ile Trp
20

( 2 ) INFORMATION FOR SEQ ID NO:59:

( i ) SEQUENCE CHARACTERISTICS:
        ( A ) LENGTH: 21 amino acids (B) TYPE: amino acid
(D) TOPOLOGY: linear (ii) MOLECULE TYPE: protein (xi) SEQUENCE DESCRIPTION: SEQ ID NO:59:

Cys Ser Leu Ser Ser Leu Met Asp Lys Glu Ala Val Tyr Phe Cys His
1               5                   10                  15
Leu Asp Ile Ile Trp
            20

(2) INFORMATION FOR SEQ ID NO:60:

(i) SEQUENCE CHARACTERISTICS:
    (A) LENGTH: 21 amino acids
    (B) TYPE: amino acid
    (D) TOPOLOGY: linear (ii) MOLECULE TYPE: protein (xi) SEQUENCE DESCRIPTION: SEQ ID NO:60:

Cys Ser Leu Ser Ser Leu Met Asp Lys Glu Leu Val Tyr Phe Cys His
1               5                   10                  15
Leu Asp Ile Ile Trp
            20

(2) INFORMATION FOR SEQ ID NO:61:

(i) SEQUENCE CHARACTERISTICS:
    (A) LENGTH: 21 amino acids
    (B) TYPE: amino acid
    (D) TOPOLOGY: linear (ii) MOLECULE TYPE: protein (xi) SEQUENCE DESCRIPTION: SEQ ID NO:61:

Cys Ser Cys Ser Ser Leu Met Asp Lys Glu Cys Val Tyr Phe Cys His
1               5                   10                  15
Leu Ile Ile Ile Trp
            20

(2) INFORMATION FOR SEQ ID NO:62:

(i) SEQUENCE CHARACTERISTICS:
    (A) LENGTH: 20 amino acids
    (B) TYPE: amino acid
    (D) TOPOLOGY: linear (ii) MOLECULE TYPE: protein (xi) SEQUENCE DESCRIPTION: SEQ ID NO:62:

Cys Ser Ala Ser Ser Leu Met Asp Lys Glu Ala Val Tyr Phe Cys Leu
1               5                   10                  15
Asp Ile Ile Trp
        20